(12) United States Patent
Alpert et al.

(10) Patent No.: US 11,109,819 B2
(45) Date of Patent: Sep. 7, 2021

(54) SYSTEM AND METHOD FOR QUANTITATIVELY MAPPING MITOCHONDRIAL MEMBRANE POTENTIAL

(71) Applicant: The General Hospital Corporation, Boston, MA (US)

(72) Inventors: Nathaniel M. Alpert, Plymouth, MA (US); Georges El Fakhri, Boston, MA (US); Nicola Guehl, Boston, MA (US); Marc Normandin, Boston, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 379 days.

(21) Appl. No.: 16/092,650

(22) PCT Filed: Apr. 10, 2017

(86) PCT No.: PCT/US2017/026750
§ 371 (c)(1),
(2) Date: Oct. 10, 2018

(87) PCT Pub. No.: WO2017/180492
PCT Pub. Date: Oct. 19, 2017

(65) Prior Publication Data
US 2019/0125281 A1    May 2, 2019

Related U.S. Application Data

(60) Provisional application No. 62/320,691, filed on Apr. 11, 2016.

(51) Int. Cl.
*A61B 6/03* (2006.01)
*A61B 6/00* (2006.01)
(Continued)

(52) U.S. Cl.
CPC ............ *A61B 6/037* (2013.01); *A61B 5/0035* (2013.01); *A61B 5/055* (2013.01); *A61B 6/4417* (2013.01);
(Continued)

(58) Field of Classification Search
CPC ....... A61B 6/037; A61B 6/503; A61B 5/0035; A61B 5/055; A61B 6/12; A61B 6/4417;
(Continued)

(56) References Cited

U.S. PATENT DOCUMENTS

2005/0260130 A1    11/2005    Elmaleh et al.
2010/0274500 A1    10/2010    Deutsch et al.
(Continued)

OTHER PUBLICATIONS

Bandula et al., Measurement of Myocardial Extracellular Volume Fraction by Using Equilibrium Contrast-Enhanced CT: Validation Against Histologic Findings, Radiology, 2013, 269(2):396-403.
(Continued)

*Primary Examiner* — Mark D Remaly
(74) *Attorney, Agent, or Firm* — Quarles & Brady LLP

(57) ABSTRACT

A system, and method, for quantitatively mapping of mitochondrial membrane potential of a tissue in a subject is provided. In some aspects, the provided method includes administering to the subject a detectably effective amount of a tracer as an emission tomography imaging agent; acquiring, using an emission tomography system, emission tomography data associated with the tissue; analyzing the emission tomography data to determine a concentration distribution of the tracer within the tissue; correlating the concentration distribution of the tracer with the membrane potential of the tissue; determining, using the correlating step, a membrane potential distribution of the tissue; and generating a report indicating the membrane potential distribution of the tissue.

20 Claims, 11 Drawing Sheets

(51) Int. Cl.
| | |
|---|---|
| *A61K 51/04* | (2006.01) |
| *G01N 33/50* | (2006.01) |
| *A61B 5/00* | (2006.01) |
| *A61B 5/055* | (2006.01) |
| *A61B 6/12* | (2006.01) |
| *G01R 33/48* | (2006.01) |

(52) U.S. Cl.
CPC .............. *A61B 6/486* (2013.01); *A61B 6/503* (2013.01); *A61B 6/504* (2013.01); *A61B 6/5217* (2013.01); *A61B 6/5235* (2013.01); *A61B 6/5247* (2013.01); *A61K 51/04* (2013.01); *A61K 51/0474* (2013.01); *G01N 33/5079* (2013.01); *A61B 6/12* (2013.01); *G01R 33/481* (2013.01)

(58) Field of Classification Search
CPC ....... A61B 6/486; A61B 6/504; A61B 6/5217; A61B 6/5235; A61B 6/5247; A61K 51/04; A61K 51/0474; G01N 33/5079; G01R 33/481; G16H 50/30
See application file for complete search history.

(56) References Cited

U.S. PATENT DOCUMENTS

| | | |
|---|---|---|
| 2013/0064768 A1 | 3/2013 | Menon et al. |
| 2013/0064769 A1 | 3/2013 | Cesati et al. |
| 2015/0132222 A1 | 5/2015 | Conti et al. |

OTHER PUBLICATIONS

Carson et al., Comparison of Bolus and Infusion Methods for Receptor Quantitation: Application to [18F] Cyclofoxy and Positron Emission Tomography, Journal of Cerebral Blood Flow & Metabolism, 1993, 13(1):24-42.

Fahmy et al., Integration of Positron Emission Tomography/Computed Tomography with Electroanatomical Mapping: A Novel Approach for Ablation of Scar-Related Ventricular Tachycardia, Heart Rhythm, 2008, 5(11):1538-1545.

Fukuda et al., Use of 11 C-triphenylmethylphosphonium for the Evaluation of Membrane Potential in the Heart by Positron-Emission Tomography, European Journal of Nuclear Medicine, 1986, 11(12):478-483.

Gao et al., Effects of Hypoxia on Relationships Between Cytosolic and Mitochondrial NAD (P) H Redox and Superoxide Generation in Coronary Arterial Smooth Muscle, American Journal of Physiology-Heart and Circulatory Physiology, 2008, 295(3):H978-H989.

Giuly et al., Method: Automatic Segmentation of Mitochondria Utilizing Patch Classification, Contour Pair Classification, and Automatically Seeded Level Sets, BMC Bioinformatics, 2012, 13:29, 12 pages.

Gurm et al., 4-[18F]-Tetraphenylphosphonium as a PET Tracer for Myocardial Mitochondrial Membrane Potential, JACC: Cardiovascular Imaging, 2012, 5(3):285-292.

Huisman et al., Initial Characterization of an 18F-Labeled Myocardial Perfusion Tracer, The Journal of Nuclear Medicine, 2008, 49(4):630-636.

Iwai et al., Electrophysiology of Cardiac Arrhythmias, 2013, In: Rosendorff C. (ed.), Essential Cardiology, Springer, New York, NY, pp. 261-275.

Janse et al., Electrophysiological Mechanisms of Ventricular Arrhythmias Resulting from Myocardial Ischemia and Infarction, Physiological Reviews, 1989, 69(4):1049-1169.

Kadenbach et al., The Role of Mitochondrial Membrane Potential in Ischemic Heart Failure, Mitochondrion, 2011, 11(5):700-706.

Kauppinen, Proton Electrochemical Potential of the Inner Mitochondrial Membrane in Isolated Perfused Rat Hearts, as Measured by Exogenous Probes, Biochimica et Biophysica Acta, 1983, 725(1):131-137.

Kettering et al., Catheter Ablation of Ventricular Tachycardias in Patients with Ischemic Cardiomyopathy: Validation of Voltage Mapping Criteria for Substrate Modification by Myocardial Viability Assessment Using FDG PET, Clinical Research in Cardiology, 2010, 99(11):753-760.

Lanoue et al., Regulation of the Uncoupling Protein in Brown Adipose Tissue, Journal of Biological Chemistry, 1986, 261(1):298-305.

Logan, et al., Graphical Analysis of Reversible Radioligand binding from Time-Activity Measurements Applied to [N—11C-methyl]-(–)-Cocaine PET Studies in Human Subjects, Journal of Cerebral Blood Flow and Metabolism, 1990, 10:740-747.

Madar et al., Characterization of Membrane Potential-Dependent Uptake of the Novel PET Tracer 18 F-fluorobenzyl triphenylphosphonium Cation, European Journal of Nuclear Medicine and Molecular Imaging, 2007, 34(12):2057-2065.

Hazel et al., Stochastic Modeling of Calcium in 3D Geometry, Biophysical Journal, 2009, 96:1691-1706.

Mitchell, Chemiosmotic Coupling in Oxidative and Photosynthetic Phosphorylation, Biochimica et Biophysica Acta, 2011, 1807:1507-1538.

Rottenberg, Membrane Potential and Surface Potential in Mitochondria: Uptake and Binding of Lipophilic Cations, The Journal of Membrane Biology, 1984, 81(2):127-138.

Rajaputra et al., Synthesis and in Vitro Biological Evaluation of Lipophilic Cation Conjugated Photosensitizers for Targeting Mitochondria, Bioorganic & Medicinal Chemistry, 2013, 21(2):379-387.

Ritchie, A Critical Assessment of the Use of Lipophilic Cations as Membrane Potential Probes, Progress in Biophysics and Molecular Biology, 1984, 43(1):1-32.

Roujol et al., 3D Late Gadolinium Enhancement in a Single Prolonged Breath-hold Using Supplemental Oxygenation and Hyperventilation, Magnetic Resonance in Medicine, 2014, 72(3):850-857.

Rugolo et al., Monitoring of the Mitochondrial and Plasma Membrane Potentials in Human Fibroblasts by Tetraphenylphosphonium Ion Distribution, Journal of Bioenergetics and Biomembranes, 1987, 19(6):705-718.

Scaduto Jr et al., Measurement of Mitochondrial Membrane Potential Using Fluorescent Rhodamine Derivatives, Biophysical Journal, 1999, 76(1):469-477.

Shoup et al., Evaluation of (4-[18 F] Fluorophenyl) Triphenylphosphonium Ion. A Potential Myocardial Blood Flow Agent for PET, Molecular Imaging and Biology, 2011, 13(3):511-517.

Strauss et al., Myocardial Imaging for Mitochondrial Membrane Potential, JACC: Cardiovascular Imaging, 2012, 5(3):293-296.

Strickberger et al., A Prospective Evaluation of Catheter Ablation of Ventricular Tachycardia as Adjuvant Therapy in Patients with Coronary Artery Disease and an Implantable Cardioverter-Defibrillator, Circulation, 1997, 96(5):1525-1531.

Wan et al., A Method of Determining Electrical Potential Gradient Across Mitochondrial Membrane in Perfused Rat Hearts, American Journal of Physiology—Heart and Circulatory Physiology, 1993, 265(2):H445-H452.

Wan et al., Effects of Cardiac Work on Electrical Potential Gradient Across Mitochondrial Membrane in Perfused Rat Hearts. American Journal of Physiology—Heart and Circulatory Physiology, 1993, 265(2):H453-H460.

Whalley et al., Basic Concepts in Cellular Cardiac Electrophysiology: Part I: Ion Channels, Membrane Currents, and the Action Potential, Pacing and Clinical Electrophysiology, 1995, 18(8):1556-1574.

White et al., Characterising the Myocardial Interstitial Space: The Clinical Relevance of Non-Invasive Imaging, Heart, 2012, 98(10):773-779.

Wong et al., Removal of Carcinoma Cells from Contaminated Bone Marrow Using the Lipophilic Cation Rhodamine 123, Clinical Cancer Research, 1995, 1(6):621-630.

Zhou et al., A Consistent and Efficient Graphical Analysis Method to Improve the Quantification of Reversible Tracer Binding in Radioligand Receptor Dynamic PET Studies, Neuroimage, 2009, 44(3):661-670.

(56) References Cited

OTHER PUBLICATIONS

PCT International Search Report and Written Opinion, PCT/US2017/026750, dated Jun. 28, 2017, 19 pages.

SYSTEM AND METHOD FOR QUANTITATIVELY MAPPING MITOCHONDRIAL MEMBRANE POTENTIAL

CROSS-REFERENCE TO RELATED APPLICATIONS

This application is a U.S. National Phase of PCT Application No. PCT/US2017/026750 filed on Apr. 10, 2017, which claims priority to U.S. provisional application No. 62/320,691, filed Apr. 11, 2016, the entire contents of which are incorporated herein by reference.

BACKGROUND OF THE INVENTION

The present disclosure relates to systems and methods for determining a medical condition of a patient using imaging data. More particularly, the present disclosure provides systems, methods, and devices for quantitatively mapping mitochondrial membrane potential of the subject's tissue, such as heart tissue, to determine the presence and progression of a medical condition of a subject.

Abnormalities in cellular membrane potential can cause or accompany a wide range of diseases and conditions, including myocardial pathologies such as arrhythmogenic tissue, reperfusion injury, hypertrophy, myopathy, scar and infarct. Thus, quantitative mapping of membrane potential may open several new areas of application. The use of tritiated lipophilic cations to measure mitochondrial membrane potential in cultured cells and isolated perfused rat hearts goes back several decades. However, the classical methodology is highly invasive and thus inappropriate for direct translation to human investigation.

Functional endpoints, such as blood flow or glucose utilization, have been previously used in an effort to detect injured but viable myocardium and to guide electrophysiological studies. A functional endpoint based on mitochondrial membrane potential, $\Delta\Psi_m$, will provide a new dimension of information because $\Delta\Psi_m$ summarizes the status of electron transport chain of the mitochondrion. The electron transport chain (ETC) of the mitochondrion is ultimately responsible for converting the nutrients we eat into an electrical ($\Delta\Psi_m$) and chemical ($\Delta pH$) gradient by pumping protons across the mitochondrial inner membrane, in the mitochondrial intermembrane space. Complex V of the ETC then converts ADP to ATP by letting protons cross the inner membrane back into the mitochondrial matrix. If the $\Delta\Psi_m$ remains within the physiological range, a small amount of reactive oxygen species (ROS) is produced. However, in mitochondrial dysfunction, impairment of ATP production is accompanied by increased ROS release, and $\Delta\Psi_m$ falls outside the narrowly regulated range. Because mitochondria are the most important source of energy and ROS in the cell, mitochondrial dysfunction is at the core of many diseases, including myopathies, diabetes, degenerative diseases, inflammation, and cardiac arrhythmias. Currently, noninvasive methods are not available for assessing mitochondrial status at the tissue level.

There is abundant and convergent evidence supporting the idea that a class of lipophilic, cationic tracers with the phosphonium motiff distribute in accord with the membrane potential. The previous use of tetraphenylphosphonium (TPP) as a probe of the electrochemical gradient and as a reference measurement of mitochondrial membrane potential supports the basic validity of PET measurements with $^{18}$F-TPP$^+$ because of the connections with the reference methodology at the physiological, kinetic and conceptual levels.

Previous measurements in cell culture and in isolated rat heart models established $^3$H-TPP$^|$ as a reference method for bench top experiments. These isolated rat heart measurements are a close relative of modern PET measurements. The major difference is that the isolated rat heart model allows access to the arterial inflow and venous outflow, making it possible to compute the tissue concentration history by the Fick principle. The kinetic curve of $^3$H-TPP$^+$ is analyzed by relating the ratio of the inward and outward transport rates to the mitochondrial membrane potential and other physiological parameters.

Nonradioactive TPP$^+$-sensitive electrodes have also been developed and validated for quantitative measurement of mitochondrial membrane potential. These measurements also analyze the kinetics of small amounts of TPP$^+$ which are allowed to permeate the cellular and its mitochondrial membranes.

TPP$^+$ had effectively been forgotten until the last decade when researchers resurrected the TPP$^+$ idea with fluorinated pluriphenylphosphonium molecules for cardiac imaging. But interestingly, the possibilities for quantitative mapping of MP were not fully appreciated at the time and TPP$^+$ was considered a blood flow imaging agent, even though no supporting evidence has been presented. Nevertheless, the previous researchers' work, as well as commercial interest has provided the safety profile needed for future human studies. PET studies of membrane potential in pigs with $^{18}$F-TPP$^+$ were previously reported and recent deeper analyses have provided more rigorous methods for quantitative mapping of $\Delta\Psi_m$ with $^{18}$F-TPP$^+$.

Given the above, there is a need for quantitatively mapping of mitochondrial membrane potential in a tissue of a subject. In addition, there is a need for in vivo quantitatively mapping of mitochondrial membrane potential to evaluate a medical condition of a subject.

SUMMARY OF THE INVENTION

The present disclosure provides a system and method for quantitatively mapping mitochondrial membrane potential in a tissue. In some aspects, the present approach may be specifically to in vivo tissue (e.g., a beating heart) of a subject, which overcomes the drawbacks of aforementioned technologies.

In one aspect of the disclosure, a method for quantitatively mapping membrane potential of a tissue in a subject is provided. In one implementation, a method for quantitatively mapping mitochondrial membrane potential of an in vivo tissue (e.g., a beating heart) in a subject is provided. The method comprises administering to the subject a detectably effective amount of $^{18}$F-tetraphenylphosphonium ($^{18}$F-TPP$^+$) as an emission tomography imaging agent; acquiring, using an emission tomography system, emission tomography data associated with the tissue; analyzing the emission tomography data to determine a concentration distribution of $^{18}$F-TPP$^+$ within the tissue; correlating the concentration distribution of $^{18}$F-TPP$^+$ with the mitochondrial membrane potential of the tissue, comprising the steps of: i) modeling a total volume of distribution of a plurality of spaces across the mitochondrial membrane and a cell membrane in an image voxel in relation with volume fractions of the plurality of spaces, and electrical potentials across the mitochondrial membrane and the cell membrane; and ii) acquiring, using a medical imaging system (such as T1=mapping with magnetic resonance imaging), anatomical imaging data and using the anatomical imaging data to determine volume fractions of the plurality of spaces associated with the tissue; determining, based on the correlation of step d), a membrane potential distribution of the tissue; and generating a report indicating the membrane potential distribution of the tissue.

In one implementation, the plurality of spaces includes an extracellular space and an intracellular space separated by a mitochondrial membrane wherein the extracellular space includes a plasma membrane and the intracellular space includes a mitochondrial space and a cytosolic space.

In one implementation, the volume fraction of the mitochondrial space and the electrical potential across the cell membrane are estimated.

In another aspect, a method for quantitatively mapping membrane potential of a tissue in a subject is provided. The method comprises administering to the subject a detectably effective amount of a tracer as an emission tomography imaging agent; acquiring, using an emission tomography system, emission tomography data associated with the tissue; analyzing the emission tomography data to determine a concentration distribution of the tracer within the tissue; correlating the concentration distribution of the tracer with the membrane potential of the tissue; determining, using the correlation step, a membrane potential distribution of the tissue; and generating a report indicating the membrane potential distribution of the tissue.

In one implementation, the emission tomography data acquiring step begins before the administration of the tracer and continues for a first duration of time. In one specific implementation, the first duration of time is at least about 60 minutes.

In another implementation, the emission tomography data acquiring step begins after the administration of the tracer. In one specific implementation, the emission tomography data acquiring step begins about 100 minutes after the administration of the tracer.

In yet another implementation, the tracer is a lipophilic cation. In one specific embodiment, the lipophilic cation is $^{18}$F-tetraphenylphosphonium (18F-TPP$^+$).

In yet another implementation, the tissue is selected from the group consisting of heart, skeletal muscle, liver, kidney and tumor (such as malignant carcinoma). In one specific embodiment, the tissue is an in vivo heart.

In yet another implementation, the membrane potential is a mitochondrial membrane potential.

In yet another implementation, the correlation step comprises designing a model by reconstructing the emission tomography data into at least one emission tomography image; defining a voxel in the at least one emission tomography image to include an extracellular space and an intracellular space separated by a cell membrane; defining the extracellular space to include a mitochondrial membrane; defining the intracellular space to include a mitochondrial space and a cytosolic space; assuming the tracer in a steady state within the voxel; and modeling a total volume of distribution in the voxel as a function of the electrical potential in mV across the mitochondrial membranes and the extracellular space volume. In one implementation, the model comprises $V_d = (1-f_{ECV})(f_{mito} \cdot e^{\beta(\Delta\Psi m + \Delta\Psi c)} + (1-f_{mito}) \cdot e^{\beta\Delta\Psi c}) + f_{ECV}$; wherein $V_d$ represents the total volume of distribution of the tracer in the imaging voxel; $f_{ECV}$ represents a volume fraction of the extracellular space; $f_{mito}$ represents a volume fraction of the mitochondrial space; $\Delta\Psi_m$ and $\Delta\Psi_c$ represent the electrical potential in mV across the mitochondrial and cell membranes, respectively.

In yet another implementation, the method further comprises acquiring, using a medical imaging system, anatomical imaging data and using the anatomical imaging data to determine a volume distribution of different spaces associated with the tissue. In one specific embodiment, measuring the volume fraction of the extracellular space $f_{ECV}$ is based on the anatomical imaging data. In another specific embodiment, the medical imaging system includes at least one of magnetic resonance imaging (MRI) or computed X-ray tomography (CT).

In yet another implementation, the method further comprises the steps of estimating the volume fraction of the mitochondrial space $f_{mito}$; and estimating the electrical potential across the cell membrane $\Delta\Psi c$.

In yet another implementation, the emission tomography system includes at least one of a positron emission tomography (PET) imaging system or a single photon emission computed tomography (SPECT) imaging system.

In another aspect, a method for identifying a disease condition of a subject is provided. The method comprises administering to the subject a detectably effective amount of a tracer; acquiring, using an emission tomography imaging system, emission tomography data and analyzing the emission tomography data to determine a concentration distribution of the tracer of a tissue of the subject; correlating the concentration distribution of the tracer with a membrane potential of the subject's tissue; processing the emission tomography data to generate a quantitative map of the membrane potential distribution of the subject's tissue; and generating a report indicative of the disease condition of the subject.

In one implementation, the emission tomography data acquiring step begins before the administration of the tracer and continues for a first duration of time. In one specific embodiment, the first duration of time is at least about 60 minutes.

In another implementation, the emission tomography data acquiring step begins after the administration of the tracer. In one specific embodiment, the emission tomography data acquiring step begins about 100 minutes after the administration of the tracer.

In yet another implementation, the tracer is a lipophilic cation. In one specific embodiment, the lip ophilic cation is $^{18}$F-tetraphenylphosphonium ($^{18}$F-TPP$^+$). In another specific implementation, the concentrations of $^{18}$F-TPP$^+$ across membranes of the tissue are in thermodynamic equilibrium or in a steady-state.

In yet another implementation, the tissue is selected from the group consisting of heart, skeletal muscle, liver, kidney and tumor (such as malignant carcinoma). In one specific implementation, the tissue is an in vivo heart (i.e., a beating heart).

In yet another implementation, the method further comprises correlating the concentration distribution of the tracer with a membrane potential of the subject's tissue by using an equation of $$V_d = (1-f_{ECV})(f_{mito} \cdot e^{-\beta(\Delta\Psi m + \Delta\Psi c)} + (1-f_{mito}) \cdot e^{-\beta\Delta\Psi c}) + f_{ECV},$$

wherein $V_d$ represents the total volume of distribution of the tracer in the imaging voxel; $f_{ECV}$ represents a volume fraction of the extracellular space; $f_{mito}$ represents a volume fraction of the mitochondrial space; $\Delta\Psi_m$ and $\Delta\Psi_c$ represent the electrical potential in mV across the mitochondrial and cell membranes, respectively.

In one specific implementation, the method comprises measuring and determining the volume fraction of the extracellular space using imaging data acquired by using at least one of a magnetic resonance imaging (MRI) system or a computed X-ray tomography (CT) system.

In another aspect, a system for quantitatively mapping membrane potential of a tissue in a subject is provided. The system comprises an emission imaging system configured to acquire emission data from the subject following an administration of a tracer; and a processor configured to access the emission data associated with the tissue; analyze the emission data to determine a concentration distribution of the tracer of the tissue of the subject; correlate the concentration distribution of the tracer with a membrane potential of the subject's tissue; and generate, using the correlation, a quantitative map of the membrane potential distribution of the subject's tissue.

In one implementation, the emission imaging system includes at least one of a positron emission tomography (PET) imaging system or a single photon emission computed tomography (SPECT) imaging system.

In one implementation, the system further comprises at least one of magnetic resonance imaging (MRI) or computed X-ray tomography (CT) for measuring the volume fraction of the extracellular space $f_{ECV}$.

In yet another aspect, a non-transitory, computer-readable storage medium is provided. The non-transitory, computer-readable storage medium has stored thereon instructions that, when executed by a computer processor, cause the computer processor to generate a report of quantitatively mapping membrane potential of a tissue in a subject by carrying out steps comprising acquiring, using an emission tomography system, an emission data associated with the tissue; analyzing the emission data to determine a concentration distribution of a tracer of the tissue of the subject; correlating the concentration distribution of the tracer with membrane potential across membranes of the subject's tissue; and generating, using the correlation, a quantitative map of the membrane potential distribution of the subject's tissue.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
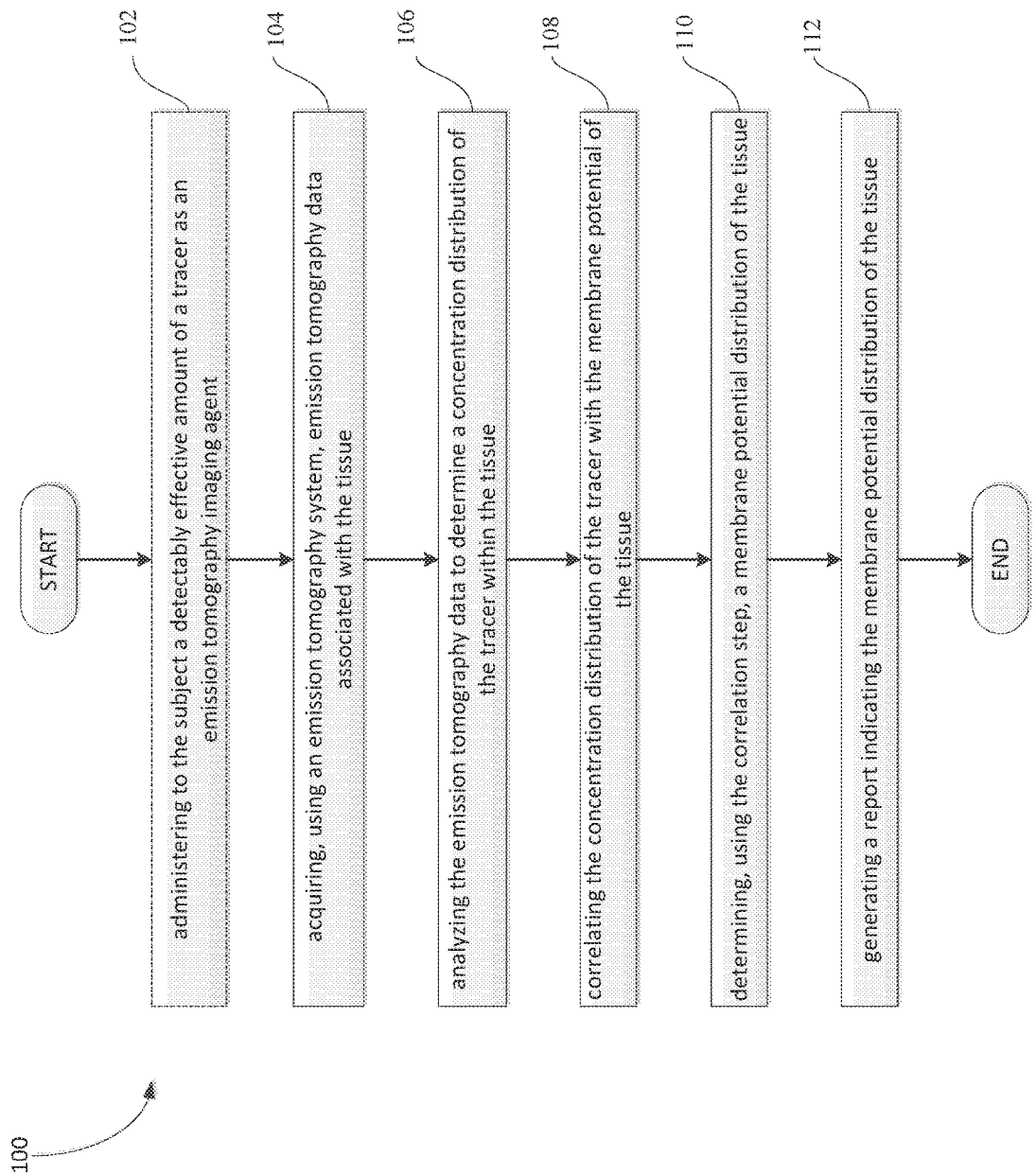
FIG. 1 is a flowchart setting forth steps of a process, in accordance with certain embodiments of the present disclosure.

The general terms used hereinbefore and hereinafter preferably have within the context of this disclosure the following meanings, unless otherwise indicated. Thus, the definitions of the general terms as used in the context of the present invention are provided herein below:

As used in this specification, the singular forms "a," "an" and "the" also encompass the plural forms of the terms to which they refer, unless the content clearly dictates otherwise.

The term "about," is used herein to mean approximately, in the region of, roughly, or around. When the term "about" is used m conjunction with a numerical range, it modifies that range by extending the boundaries above and below the numerical values set forth. In general, the term "about" is used herein to modify a numerical value above and below the stated value by a variance of ±10%.

The term "subject," as used herein, refers to an animal, preferably a mammal, most preferably a human, who is in the need of evaluation of a disease or a physical condition. The term subject may be interchangeably used with the term patient in the context of the present invention.

The term "tissue," as used herein, refers to all types of biological tissue, including organs and cells and parts thereof. In one embodiment, the tissue of the present disclosure is selected from the group consisting of heart, skeletal muscle, liver, kidney and tumor. An example of tumor is malignant carcinoma.

The term "membrane potential," as used herein, refers to the electrical potential difference between the aqueous phases separated by a membrane and will be given by the symbol ($\Delta\Psi$).

The term "mitochondrial membrane potential," as used herein, refers to the electrical potential difference between the compartments separated by the mitochondrial inner membrane, will be given by the symbol ($\Delta\Psi_m$).

The term "steady-state" or "steady-state equilibrium," as used herein, means that a contrast agent or a tracer has achieved equilibrium in the blood and/or a tissue of an animal (e.g., a human).

The term "tracer," as used herein, refers to a compound comprising a detectable signaling label. In one implementation, the tracer in the present discourse refers to a PET tracer or a SPECT tracer. The term "PET tracer" or "SPECT tracer," as used herein, refers to a compound comprising positron-emitting radioactive isotope. In one configuration, the tracer of the present disclosure is a lipophilic cation, such as $^{18}$F-tetraphenylphosphonium ($^{18}$F-TPP$^+$). Specifically, Applicants demonstrate that using $^{18}$F-TPP$^+$ as a tracer can reach a steady state in a subject rapidly and timely (within minutes, see FIG. 4 and FIG. 11) and remain in the stead state for at least 2 hours. Applicants note that US patent application No. 2013/0064768 A1 discloses other lipophilic cations such as MitoQ, DecylTPP, FluroUndecylTPP and TPMP. As shown in FIGS. 1-5, none of MitoQ, DecylTPP, FluroUndecylTPP and TPMP reach a steady state in mouse tissues within an hour, let alone remaining in a steady state for at least 2 hours.

The term "administer," as used herein, refers to any method for introducing the compositions (e.g., of a tracer) of the present invention into a subject. Typical methods include, but are not limited to, oral, intranasal, parenteral (intravenous, intramuscular, or subcutaneous), or rectal. In one configuration of the present disclosure, a pulse or bolus injection may be used. In another configuration, a constant infusion injection may be used. In yet another configuration, a combination of a pulse or bolus injection and a constant infusion injection may be used.

The term "pulse or bolus injection," as used herein, refers to the administration of a discrete amount of medication, drug or other compound in order to raise its concentration in blood to an effective level. The administration can be given by injection: intravenously; intramuscularly; intrathecally; or subcutaneously. In one configuration of the present disclosure, a pulse or bolus injection and a constant infusion used in combination to achieve constant tissue and plasma concentration (e.g., a steady-state) of a tracer such as TPP$^+$ more rapidly than can be achieved by constant infusion alone.

The term "constant infusion," as used herein, refers to a continuous administration of a fluid including a discrete amount of medication, drug or other compound to a patient or subject for an extended period of time without having to establish a new site of administration each time the fluid is administered. The detail information of both a pulse or bolus injection and a constant infusion was previously described in the literature such as *J Cereb Blood Flow Metab.*, 1993, 13(1):24-42.

The term "contrast agent," as used herein, refers to a molecule that generates a contrasting effect in vivo, whether the effect is direct or indirect or both.

The term "a detectably effective amount," as used herein, refers to an amount of a tracer or a contrast agent of the present disclosure sufficient to yield an acceptable image using an equipment which is available for clinical use. A detectably effective amount of the imaging agent of the invention may be administered in more than one injection. The detectably effective amount of the imaging agent of the invention can vary according to factors such as the degree of susceptibility of the individual, the age, sex, and weight of the individual, idiosyncratic responses of the individual, the dosimetry. Detectably effective amounts of the imaging agent of the invention can also vary according to instrument and film-related factors. Optimization of such factors is well within the level of skill in the art.

The amount of a tracer or a contrast agent used for diagnostic purposes and the duration of the imaging study may depend upon the radionuclide used to label the agent, the body mass of the patient, the nature and severity of the condition being treated, the nature of therapeutic treatments which the patient has undergone, and on the idiosyncratic responses of the patient. Ultimately, the attending physician may decide the amount of imaging agent to administer to each individual patient and the duration of the imaging study.

The present disclosure is directed to a novel approach for quantitatively mapping membrane potentials, such as mitochondrial membrane potential, using emission tomography data. Compared with other conventional methods, the approach of the present disclosure is non-invasive and applicable to an in vivo tissue such as a beating heart, liver, lung, muscle and malignant tumor.

In some aspects, the present disclosure describes a system, and method, that overcomes the drawbacks of previous technologies attempting to use blood flow tracers to assess mitochondrial membrane status. For instance, the present approach uses an emission tomography data to estimate the steady-state concentration of a cationic lipophilic tracers that distribute in accord with the mitochondrial membrane potential. In one implementation, the present approach uses a highly lipophilic cationic tracer such as $^{18}$F-TPP$^+$. Applicants demonstrated that a lipophilic cationic tracer such as $^{18}$F-TPP$^+$, reached a steady state in a tissue (e.g., an in vivo tissue) within two hours. Applicants envision other lipophilic cations with similar properties to $^{18}$F-TPP$^+$ would also be used as a tracer in the present disclosure.

In one aspect, the present disclosure reveals a method using primed constant infusion in which the subject is infused with a lipophilic cationic tracer for 90 minutes and then imaged after the tracer is in steady state within the subject.

In one aspect, the present disclosure reveals a method for quantitatively mapping membrane potential of a tissue in a subject. In one implementation, the present disclosure reveals a method for quantitatively mapping mitochondrial membrane potential of an in vivo tissue in a subject.

Many tissues may be suitable for the present method of quantitatively mapping membrane potential. In one implementation, a tissue of the present disclosure is selected from the group consisting of heart, skeletal muscle, liver, kidney and tumor such as malignant carcinoma. In one preferred configuration, the tissue is a heart, more preferably an in vivo heart (e.g., a beating heart).

In one preferred embodiment, the membrane potential is a mitochondrial membrane potential.

Referring to FIG. 1, a flowchart setting forth steps of an example process 100 of the method for quantitatively mapping membrane potentials is illustrated. The process 100 may begin with administering to the subject a detectably effective amount of a tracer as an emission tomography imaging agent, as indicated at step 102.

The tracer of the present disclosure may be selected and administered at step 102 such that its concentration reaches a steady-state in the blood and target tissue quickly when an emission tomography data associated with the tissue is acquired.

In one implementation, the tracer may include any compound or substance with a detectable signaling label. As an example, the tracer may be a cationic tracer, such as a lipophilic cationic tracer. Preferably, the cationic tracer is a radioactive-isotope-labeled lipophilic cation, such as an $^{18}$F-lipophilic cation. When lipophilic cations with delocalized charges are introduced into the plasma of a living animal, lipophilic cations cross plasma and mitochondrial membranes and accumulate in the extracellular and intracellular spaces, due to the electrochemical gradient across the plasma and mitochondrial membranes. Lipophilic cations are thus good candidates to correlate their concentration distribution derived from emission tomography data with membrane potential of a target tissue.

In some aspects, the lipophilic cation tracers of the present disclosure may include ethidium$^+$, tetraphenylphosphonium$^+$ (TPP$^+$), triphenylmethylphosphonium$^+$ (TPMP$^+$), tetraphenylarsonium$^+$ (TPA$^+$ and others.

In other aspects, the lipophilic cation tracers of the present disclosure may include porphyrin-based or rhodamine-based cations. The porphyrin-based or rhodamine-based cations may include delocalized lipophilic cation-porphyrin conjugates such as CMP-Rh (a core modified porphyrin-rhodamine B cation), CMP-tPP (a core modified porphyrin-mono-triphenyl phosphonium cation), CMP-(tPP)(2) (a core modified porphyrin-di-tPP cation) and other compounds as disclosed in *Bioorg Med Chem.* 2013, 21(2):379-87.

In yet other aspects, the lipophilic cation tracers of the present disclosure may include other rhodamine-based compounds such as rhodamine 123 as disclosed in *Clin Cancer Res.* 1995, 1(6):621-30.

In yet other aspects, the lipophilic cation tracers of the present disclosure may include fluorescent dyes. The fluorescent dyes may include other rhodamine-based compounds or rhodamine derivatives such as tetramethylrhodamine methyl ester (TMRM), and tetramethyl rhodamine ethyl ester (TMRE) as disclosed in *Biophys J.,* 1999, 76: 469-477.

Figure 4:
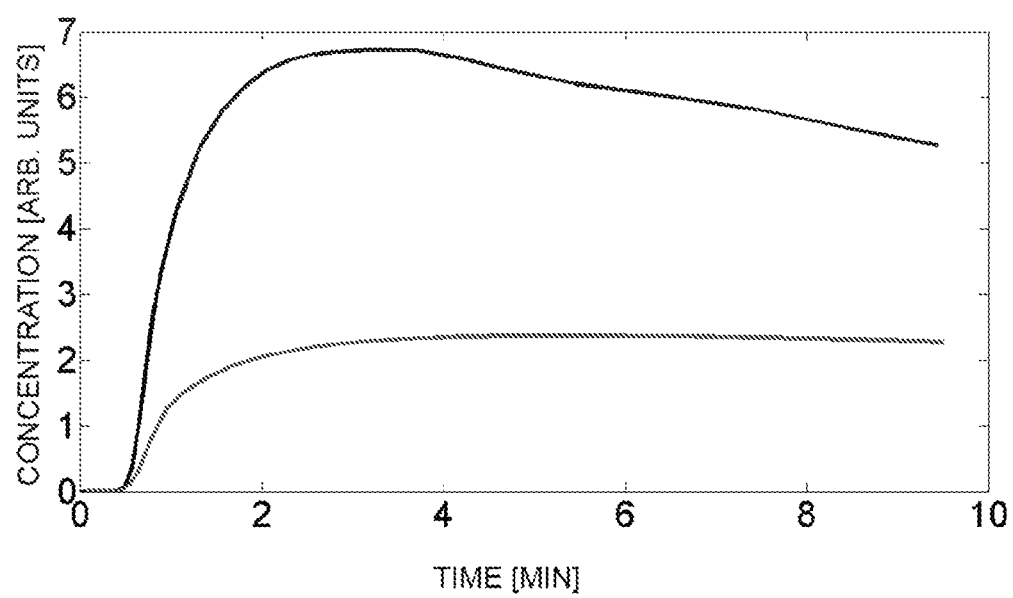
FIG. 4 is a graphical illustration depicting comparison of myocardial kinetics of TPP[i] and Flurpiridaz. The black line (the top line) depicts Flurpiridaz kinetics; whereas, the red line (the bottom line) depicts TPP$^+$ kinetics. Concentrations are normalized to remove the effect of injected radioactivity dose.

As one specific example, $^{18}$F-tetraphenylphosphonium ($^{18}$F-TPP$^+$) may be used as a cation tracer. As shown in FIG. 4, $^{18}$F-TPP$^+$ has much slower kinetics than $^{18}$F-Flurppiridaz, which is a tracer with high first pass capillary extraction (E>0.9). $^{18}$F-TPP$^+$ accumulates slowly in the myocardium. $^{18}$F-TPP$^+$ reaches a steady state in the tissues within minutes. Thus, $^{18}$F-TPP$^+$ may not provide useful myocardial flow measurements. As shown in the Examples, $^{18}$F-TPP$^+$ can be used as a steady-state tracer for quantitatively mapping membrane potential of a tissue in a subject.

In the Example and throughout the disclosure, Applicants use a cationic tracer such as $^{18}$F-TPP$^+$ for the purpose of demonstration. Applicants envision that other tracers with similar properties to $^{18}$F-TPP$^1$ may also be used for the present disclosure.

Although the amount of administration is detectable for emission tomography imaging, the concentration of the cationic tracer such as $^{18}$F-TPP$^+$ is significantly lower than the concentrations of K$^+$, Na$^+$ and Cl. For example, the in vivo K$^+$, Na$^+$ and Cl$^-$ concentrations are $10^7$-$10^{10}$ times of that of TPP$^+$. Thus, the concentrations of $^{18}$F-TPP$^+$ are so small that they cause no detectable physiological changes or biochemical perturbations of the subject.

In one implementation, the tracer such as $^{18}$F-TPP$^+$ may be administered by a pulse or bolus injection, by a constant infusion, or by a combination of both a pulse or bolus injection and a constant infusion.

In one specific embodiment, the tracer such as $^{18}$F-TPP$^+$ may be administered by a pulse or bolus injection.

In another specific embodiment, the tracer such as $^{18}$F-TPP$^+$ may be administered by a constant infusion.

In yet another specific embodiment, the tracer such as $^{18}$F-TPP$^+$ may be administered by a combination of both a pulse or bolus injection and a constant infusion. For example, $^{18}$F-TPP$^+$ may be administered by a pulse or bolus injection followed by a constant infusion. The addition of the pulse or bolus injection to the constant infusion can shorten the time needed to reach the steady state for $^{18}$F-TPP$^1$.

In one specific embodiment, a constant infusion may lead to a steady state of the tracer such as $^{18}$F-TPP$^1$ in a tissue.

In some aspects, step 102, or other steps in the process 100, may include the step of frequently evaluating the kinetic behavior of the tracer such as $^{18}$F-TPP$^+$ in a tissue. For example, arterial and/or venous blood samples may be drawn for a certain frequency. The blood samples may be centrifuged to determine plasma and red cell concentration histories. Concentration ratios of whole blood to plasma may thus computed. By monitoring the change of concentration ratios of whole blood to plasma, the kinetic behavior of the tracer such as $^{18}$F-TPP$^+$ in a tissue may be evaluated.

In one specific embodiment, arterial blood sampling of $^{18}$F-TPP$^+$ were drawn every 5, 10 or 15 seconds for the first 3 minutes, then at 15 seconds, 30 seconds or 1 minute intervals for 5 minutes, and at increasing intervals until 120 minutes post injection.

In another specific embodiment, venous several blood samples may be also drawn at 1, 2, 3, 4, 5, 10, 15, 30, 60 and 90 minutes for comparison with arterial samples.

Referring again to FIG. 1, emission tomography data associated with the tissue is acquired by using an emission tomography system, as indicated at step 104. In some embodiments, the emission tomography system may include a positron emission tomography (PET) imaging system or a single photon emission computed tomography (SPECT) imaging system.

In some aspects, kinetic behavior of the administered tracer, such 18F-TPP$^+$, may be monitored, e.g., through measuring the change of concentration ratio of whole blood to plasma.

Also, the beginning time and the duration of step 104 may depend on the administration carried out at step 102.

For example, when a tracer such as $^{18}$F-TPP$^+$ is administered by a pulse or bolus injection to a subject, emission tomography data may be acquired before the administration and continues for a first duration of time. In one embodiment, the first duration of time is at least about 60 minutes, preferably at least about 100 minutes, more preferably about 120 minutes.

When a tracer such as $^{18}$F-TPP$^+$ is administered by a combination of both a pulse or bolus injection and a constant infusion, emission tomography data may be acquired after the administration of $^{18}$F-TPP$^+$. In implementation, emission tomography data may be acquired about 80 minutes, preferably about 90 minutes, more preferably about 100 minutes after the administration of $^{18}$F-TPP$^+$.

Thus, the administration step 102 may be not necessary. For example, a subject may be pre-administrated with $^{18}$F-TPP$^+$ by a pulse or bolus injection followed by a constant infusion. The subject may choose to be present before the emission tomography system after about 80 minutes, preferably about 90 minutes, more preferably about 100 minutes after the administration of $^{18}$F-TPP$^+$. As such, the method for quantitatively mapping membrane potentials may start with step 104.

Referring again to FIG. 1, the emission tomography data is analyzed to determine a concentration distribution of the tracer within the tissue, as indicated at step 106.

In one specific embodiment, the emission tomography data such as dynamic PET data may be analyzed by using Logan plot (*J Cereb Blood Flow Metab*, 1990, 10: 740-747). Parametric images of the tracer such as $^{18}$F-TPP$^+$ volume of distribution, $V_d$ may be produced and reoriented into the short axis or other various projections.

In some aspects, when $V_d$ is calculated, the plasma concentration may be directly estimated from the PET scans by sampling the specific location with a region of interest (ROI). As such, a quantitative map of volume of distribution $V_d$ of a tissue may be produced.

Figure 8:
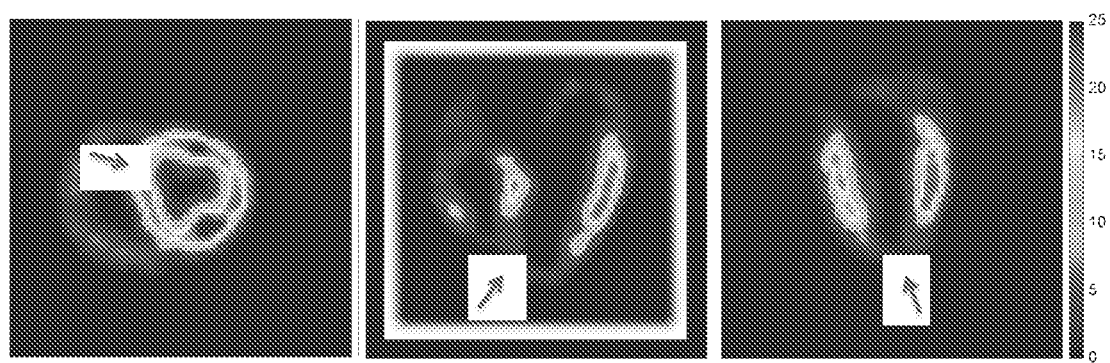
FIG. 8 is a set of photos showing a quantitative map of volume of distribution $V_d$ of an injured pig in the short axis, horizontal axis and vertical long axis (left to right), formed in accordance with certain aspects of the present disclosure. Red arrows indicate location of the injury.

For example, FIG. 8 shows a quantitative map of volume of distribution $V_d$ of an injured pig in the short axis, horizontal axis and vertical long axis (left to right). Red arrows in FIG. 8 indicate location of the injury.

Referring again to FIG. 1, the concentration distribution of the tracer such as $^{18}$F-TPP$^+$ is correlated with the membrane potential of the tissue, as indicated at step 108.

The correlation step 108 is based on the theory that estimates of $\Delta\Psi_m$ obtained with a tracer such as $^{18}$F-TPP$^+$ rely on the Nernst equation, which relates $\Delta\Psi_m$ in terms of the concentration ratio inside of versus outside of the membrane.

In one configuration, the correlation at step 108 comprises the steps of i) modeling a total volume of distribution of a plurality of spaces across the mitochondrial membrane and a cell membrane in an imaging voxel in relation with volume fractions of the plurality of spaces, and electrical potentials across the mitochondrial membrane and the cell membrane; and ii) acquiring, using a medical imaging system, anatomical imaging data and using the anatomical imaging data to determine volume fractions of the plurality of spaces associated with the tissue.

Figure 5:
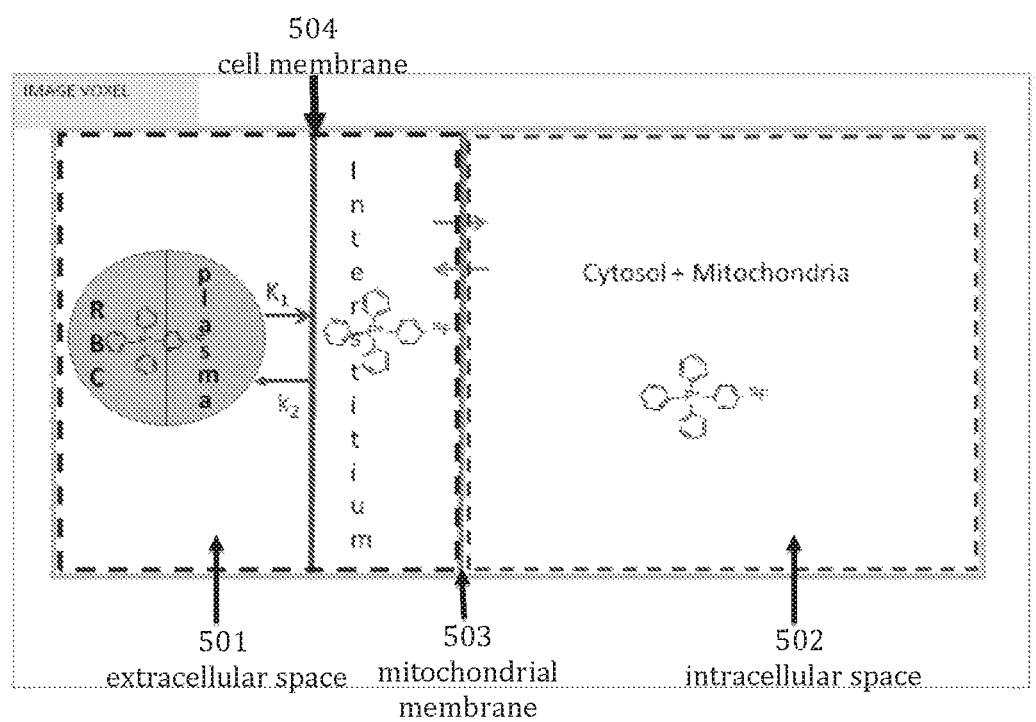
FIG. 5 is a schematic diagram depicting concentration distribution of a tracer within a conceptual emission image voxel, in accordance with certain embodiments of the present disclosure.

FIG. 5 shows a schematic diagram depicting concentration distribution of a tracer within a conceptual emission image voxel. As shown in FIG. 5, a conceptual emission image voxel may include an extracellular space 501 and an intracellular space 502 separated by a mitochondrial membrane 503. The extracellular space may include a plasma membrane (or a cell membrane) 504. Further, the intracellular space may include a mitochondrial space and a cytosolic space.

In one configuration, the plurality of spaces may include an extracellular space and an intracellular space separated by a mitochondrial membrane wherein the extracellular space includes a plasma membrane and the intracellular space includes a mitochondrial space and a cytosolic space.

In some implementations, the correlation step 108 may include the steps of i) modeling a total volume of distribution of the tracer across the mitochondrial membrane and a cell membrane in an imaging voxel in relation with volume fractions of the extracellular space and the mitochondrial space, and electrical potentials across the mitochondrial membrane and the cell membrane; and ii) acquiring, using a medical imaging system, anatomical imaging data and using the anatomical imaging data to determine the volume fraction of the extracellular space associated with the tissue.

In one implementation, the volume fraction of the mitochondrial space and the electrical potential across the cell membrane may be estimated.

The correlation step 108 may include steps of designing or generating a model by reconstructing the emission tomography data into at least one emission tomography image; defining a voxel in the at least one emission tomography image to include an extracellular space and an intracellular space separated by a cell membrane; defining the extracellular space to include a mitochondrial membrane; defining the intracellular space to include a mitochondrial space and a cytosolic space; assuming the tracer in a steady state within the voxel; and modeling a total volume of distribution in the voxel as a function of the electrical potential, for example in mV, across the mitochondrial membranes and the extracellular space volume.

As shown in FIG. 5, a voxel in the at least one emission tomography image may include an extracellular space and an intracellular space separated by a mitochondrial membrane. The extracellular space may include a plasma membrane. Further, the intracellular space may include a mitochondrial space and a cytosolic space. The total concentration for the tissue volume can be represented by Equation 1:

$$C_{PET}=(1-f_{ECV})(f_{mito}C_{mito}+(1-f_{mito})\cdot C_{cyto})+ f_{ECV}\cdot C_{ECV} \quad (b\ 1),$$

wherein $f$ denotes a volume fraction and subscripts $_{cell}$ and $_{ECV}$ refer to the cellular and extracellular volume components respectively. The cellular component can be approximated as the sum of mitochondrial ($_{mito}$) and cytosolic ($_{cyto}$) fractions.

By assuming the tracer reaches a steady state within the voxel, thus $$C_{ECV}=C_{PET} \quad (2)$$

By incorporating the Nernst equation into Equations 1 and 2, the total volume of distribution in a PET voxel can be expressed as Equation 3:

$$V_d=(1-f_{ECV})(f_{mito}e^{-\beta(\Delta\Psi m+\Delta\Psi c)}+(1-f_{mito})\cdot e^{-\beta\Delta\Psi c})+f_{ECV} \quad (3),$$

wherein $V_d$ represents the total volume of distribution of the tracer in the imaging voxel; $f_{ECV}$ represents a volume fraction of the extracellular space; $f_{mito}$ represents a volume fraction of the mitochondrial space; $\Delta\Psi m$ and $\Delta\Psi c$ represent the electrical potential in mV across the mitochondrial and cell membranes, respectively; $\beta=zF/RT$ is a ratio of known physical parameters: F denotes Faraday's constant, z is the valence, R is the universal gas constant and T is the temperature in degrees Kelvin.

In some implementations, the correlation step 108 further includes acquiring, using a medical imaging system, anatomical imaging data and using the anatomical imaging data to determine a volume distribution of different spaces associated with the tissue. The medical imaging system may be a magnetic resonance imaging (MRI) system, a computed X-ray tomography (CT) system, or other imaging system.

In some implementations, the correlation step 108 includes measuring the volume fraction of the extracellular space $f_{ECV}$ based on the anatomical imaging data of MRI or CT. The Example shows the detail information for measuring and determining the volume fraction of the extracellular space $f_{ECV}$ based on the anatomical imaging data of MRI or CT.

In one configuration, the MRI or CT imaging data may be acquired and/or processed to quantitatively correspond to that of the PET data. For example, CT images may be resliced to match the PET voxel size and smoothed before calculation of the ECV fraction.

The Example demonstrates measurements of the fractional ECV by using CT scanning data. Specifically, the ECV fraction may be calculated as Equation 4:

$$ECV=(1-H_{ct})\cdot[(HU_{post}-HU_{pre})_{tissue}/[(HU_{post}-HU_{pre})_{pre}] \quad (4)$$

where $HU_{post}$ and $HU_{pre}$ are the CT numbers in Hounsfield units, post- and pre-contrast, respectively.

Referring again to FIG. 1, by carrying out the correlating step 108 as discussed above, a membrane potential distribution of the tissue may then be determined, as indicated at step 110.

As shown in Equation 3, $V_d$ can be measured directly from emission tomography data such as PET data. The membrane potential distribution $\Delta\Psi_m$ can be determined if the values of the volume fractions ($f_{ECV}$ and $f_{mito}$) and the cellular membrane potential ($\Delta\Psi c$) are available.

In one implementation, values of the volume fraction of the mitochondrial space $f_{mito}$ and the cellular membrane potential $\Delta\Psi c$ may be estimated. For instance, $\Delta\Psi c = -30$ mV and $f_{mito} = 0.15$. Applicants envision that other estimated $\Delta\Psi c$ and $f_{mito}$ may be used, e.g., for different tissues.

The parametric maps of $V_d$ may be converted to maps of $\Delta\Psi_m$ by using Equation 5:

$$\Delta\Psi = \Delta\Psi_m + \Delta\Psi_c = \frac{1}{\beta}\log\left[\frac{V_d - f_{xcell} - (1 - f_{xcell})(1 - f_m)e^{\beta\Delta\Psi_c}}{f_m(1 - f_{xcell})}\right] \quad (5)$$

In the calculation of $V_d$, the plasma concentration may be directly estimated from the PET scans by measuring signals from the left ventricle (LV) chamber. A quantitative maps of $V_d$ may be produced. FIG. 8 shows a quantitative map of volume of distribution $V_d$ of an injured pig in the short axis, horizontal axis and vertical long axis.

Figure 9:
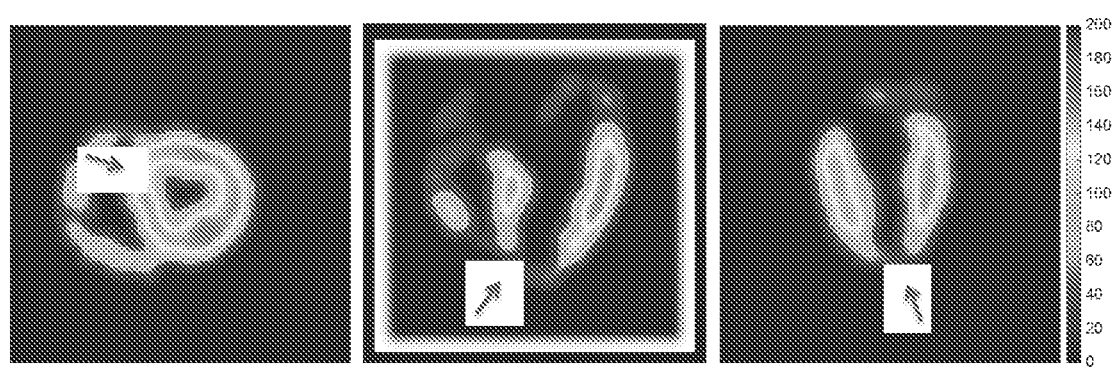
FIG. 9 is a set of photos showing a quantitative map of membrane potential $\Delta\Psi_m$ of an injured pig in the short axis, horizontal axis and vertical long axis (left to right), formed in accordance with certain aspects of the present disclosure. Red arrows indicate location of the injury.

Since estimates for the volume fractions and cellular membrane potential are available, a quantitative map of volume of distribution $V_d$ may be converted into a quantitative map of $\Delta\Psi_m$ by using Equation 5. FIG. 9 shows a quantitative map of membrane potential $\Delta\Psi_m$ of an injured pig in the short axis, horizontal axis and vertical long axis (left to right), corresponding to FIG. 8.

Referring again to FIG. 1, a report may then be generated, as indicated at step 110. The report may be in any form and include any information. For instance, the report may indicate determined membrane potential distributions, or changes thereof, for imaged tissues. The report may also include imaging showing anatomical and quantitative maps. For instance, the report may include maps of membrane potential $\Delta\Psi_m$ of imaged tissues.

In another aspect, the present disclosure reveals a method for identifying a disease condition of a subject. In one configuration, the present disclosure reveals a method for identifying a disease condition of a subject by quantitatively mapping membrane potentials (e.g., mitochondrial membrane potentials $\Delta\Psi_m$) of tissues of the subject. When myocytes experience infarction or ischemia, there is either complete or partial depolarization of those cells, resulting in a reduced membrane potential. When the cell is partially depolarized, action potentials are distorted, causing local changes in rhythm, or disruptions or blockage of conductance and arrhythmia. Thus, a disease condition of a subject may be determined by mapping and monitoring the changes of membrane potentials $\Delta\Psi$.

In one implementation, the disease condition may include myocardial pathologies such as arrhythmogenic tissue, reperfusion injury, hypertrophy, myopathy, scar and infarct.

Figure 2:
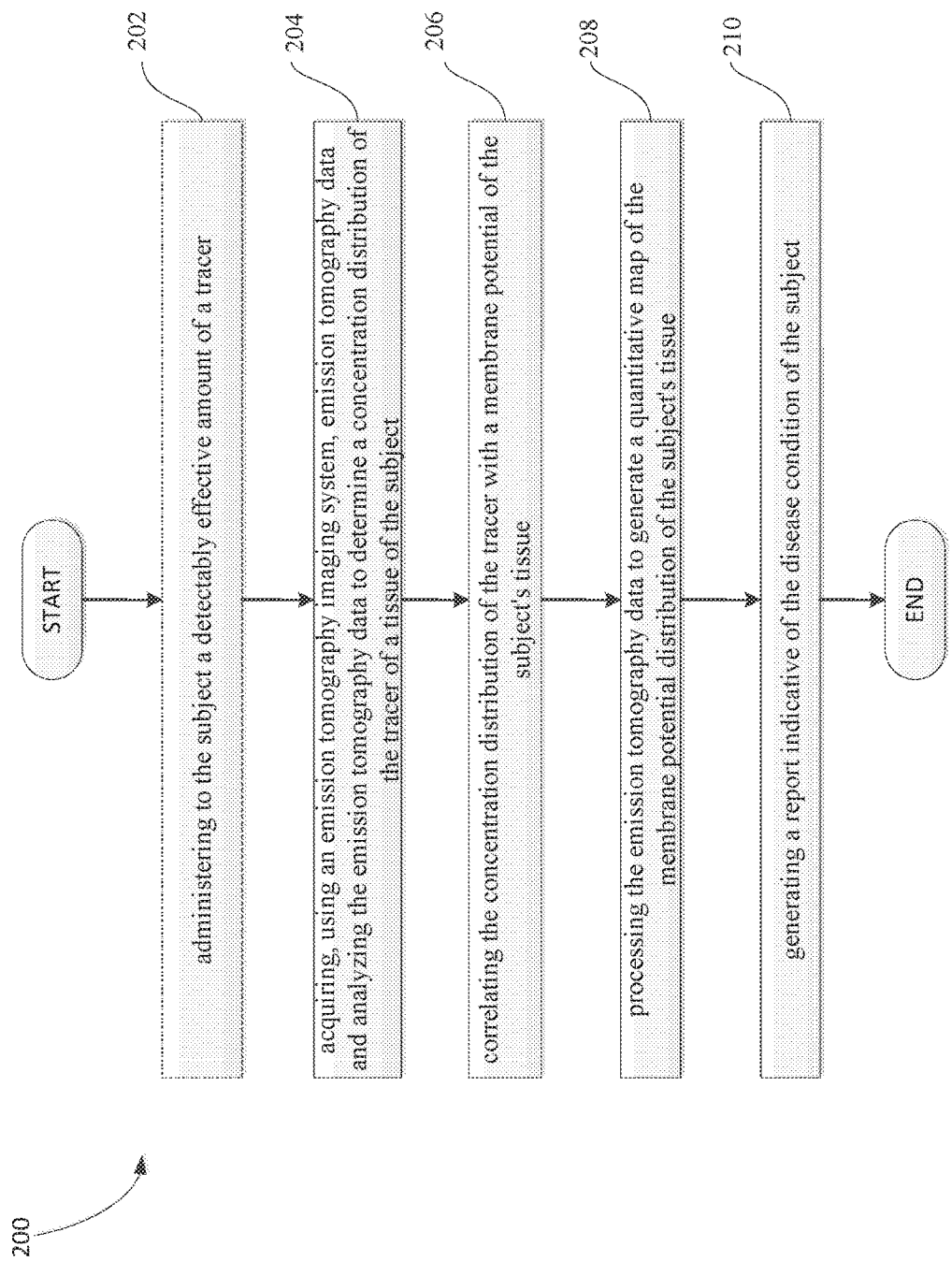
FIG. 2 is a flowchart setting forth steps of a process, in accordance with certain embodiments of the present disclosure.

Referring now to FIG. 2, the method for identifying a disease condition of a subject starts with administering to the subject a detectably effective amount of a tracer, as indicated at step 202.

In one implementation, the tracer is a cationic tracer. In one implementation, the cationic tracer is a lipophilic cation such as $^{18}$F-TPP$^+$. In one implementation, the concentrations of $^{18}$F-TPP$^+$ across membranes of the tissue are in thermodynamic equilibrium or in a steady state. Any method as discussed herein may be used to administer the tracer such as $^{18}$F-TPP$^+$. For example, the tracer such as $^{18}$F-TPP$^+$ may be administered by a pulse or bolus injection, by a constant infusion, or by a combination of both a pulse or bolus injection and a constant infusion.

Referring to FIG. 2, emission tomography data is acquired by using an emission tomography imaging system and analyzed to determine a concentration distribution of the tracer of a tissue of the subject, as indicated at step 204. In one embodiment, the tissue is selected from the group consisting of heart, skeletal muscle, liver, kidney and tumor such as malignant carcinoma. In one preferred embodiment, the tissue is a heart, more preferably an in vivo heart (e.g., a beating heart).

In one implementation, the emission tomography system includes at least one of a positron emission tomography (PET) imaging system or a single photon emission computed tomography (SPECT) imaging system. By way of example, the emission tomography system is a PET imaging system.

As discussed above, the beginning time and the duration of step 204 depends on the manner of the administration of step 202.

For example, when $^{18}$F-TPP$^+$ is administered by a pulse or bolus injection to a subject, emission tomography data may be acquired before the administration and continues for a first duration of time. In one implementation, the first duration of time is at least about 60 minutes, preferably at least about 100 minutes, more preferably about 120 minutes.

When a tracer such as $^{18}$F-TPP$^i$ is administered by a combination of both a pulse or bolus injection and a constant infusion, emission tomography data may be acquired after the administration of the tracer such as $^{18}$F-TPP$^+$. In one implementation, emission tomography data may be acquired about 80 minutes, preferably about 90 minutes, more preferably about 100 minutes after the administration of the tracer such as $^{18}$F-TPP$^+$.

As discussed above, the administration step (202) may be not necessary. In one configuration, the method for quantitatively mapping membrane potentials may start with step 204.

The emission tomography data such as dynamic PET data may be analyzed by using Logan plot as discussed above. Parametric images of the $^{18}$F-TPP$^+$ volume of distribution, $V_d$ may be produced and reoriented into the short axis or other various projections. A quantitative map of volume of distribution $V_d$ of a tissue may be further produced.

Referring to FIG. 2, the concentration distribution of the tracer is correlated with a membrane potential of the subject's tissue, as indicated at step 206.

As discussed above, the correlation may include the steps of i) modeling a total volume of distribution of the tracer across the mitochondrial membrane and a cell membrane in an imaging voxel in relation with volume fractions of the extracellular space and the mitochondrial space, and electrical potentials across the mitochondrial membrane and the cell membrane; and ii) acquiring, using a medical imaging system, anatomical imaging data and using the anatomical imaging data to determine the volume fraction of the extracellular space associated with the tissue.

By following the same theory, assumption and estimation as discussed above, the total volume of distribution in a PET voxel for a method of identifying a disease condition of a subject can be expressed as Equation 3.

In one implementation, the correlation step 206 further comprises measuring the volume fraction of the extracellular space using imaging data acquired using at least one of a magnetic resonance imaging (MRI) system or a computed X-ray tomography (CT) system.

Referring to FIG. 2, the emission tomography data is processed to generate a quantitative map of the membrane potential distribution of the subject's tissue, as indicated at step 208.

Specifically, the parametric maps of $V_d$ may be converted to maps of $\Delta\Psi_m$ by using Equation 5 as discussed above, because values of the volume fraction of the mitochondrial space $f_{mito}$ and the cellular membrane potential $\Delta\Psi_c$ may be estimated (e.g., $\Delta\Psi_c=-30$ mV and $f_{mito}=0.15$ for heart).

Referring to FIG. 2, the method for identifying a disease condition of a subject ends with generating a report indicating the disease condition of the subject, as indicated at step 210. In one implementation, the report may also include imaging showing a quantitative map of membrane potential $\Delta\Psi_m$ of the tissue.

When a tissue such as a heart in a disease condition and myocytes experience infarction or ischemia, there is either complete or partial depolarization of those cells, resulting in a reduced membrane potential. Thus, a disease condition of a subject can be derived from any abnormality of membrane potential mapping.

In one implementation, the present method for identifying a disease condition may be independently used.

In another implementation, the present method for identifying a disease condition may be combined with other mapping technical such as electroanatomic mapping (EAM). For example, maps of $\Delta\Psi_m$ could be obtained prior to EAM and serve as a road map for the electrophysiologist, allowing more detailed investigation. Unlike EAM, which is sensitive to current flowing near the surfaces of the myocardium, the PET method is sensitive to abnormalities in $\Delta\Psi_m$ at any depth in myocardial thickness.

In another aspect, the present disclosure reveals a PET system configured to produce a quantitative map of membrane potential $\Delta\Psi_m$ of a tissue of a subject.

Figure 3:
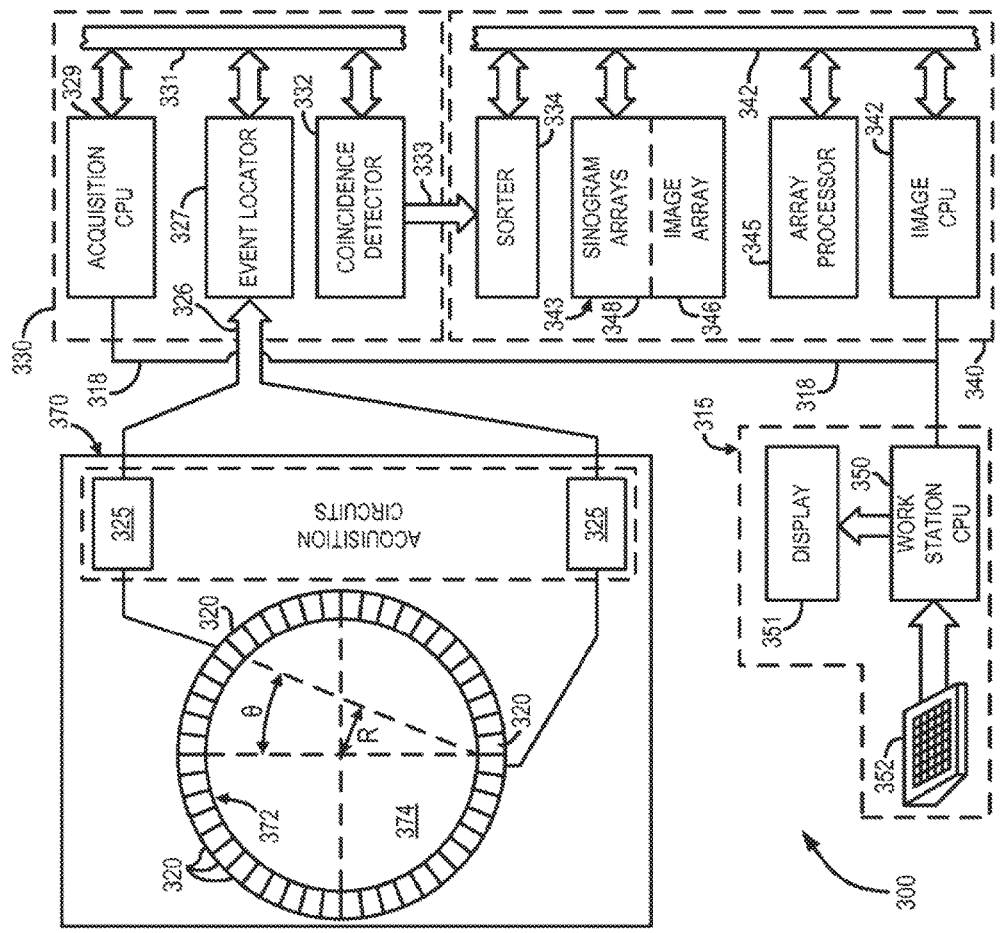
FIG. 3 is a schematic diagram depicting an emission tomography system, in accordance with certain embodiments of the present disclosure.

Referring particularly to FIG. 3, a schematic diagram of a PET system 300 is shown. Although PET system 300, as represented in the example of FIG. 3, can be implemented as a stand-alone imaging system, in accordance with some aspects of the present disclosure, it may be appreciated that PET system 300 may also utilized in combination with other imaging systems. For example, PET system 300 may be integrated into a multi-modality, or hybrid, imaging system, such as a PET/CT system, or a PET/MR system. In some aspects, raw or processed PET data, or images, generated using PET system 300 may be directly used to generate photon attenuation maps, and/or attenuation-corrected images. In other aspects, raw or processed PET data, or images, may be combined with information from other raw or processed data or images, such as CT or MR data or images, to generate photon attenuation maps, and/or attenuation-corrected images.

In one aspect, the present disclosure reveals a PET/CT system, or a PET/MR system for quantitatively mapping membrane potential of a tissue in a subject. In one implementation, the present disclosure reveals a PET/CT system, or a PET/MR system for quantitatively mapping mitochondrial membrane potential of an in vivo tissue in a subject. The example shows the data obtained from a PET/CT system, or a PET/MR system.

As illustrated in FIG. 3, PET system 300 includes a gantry 370, which supports a detector ring assembly 372. The detector ring 372 includes detector units 320. The signals produced by the detector units 320 are then received by a set of acquisition circuits 325, which produce digital signals indicating the line of response and the total energy. These signals are sent through a communications link 326 to an event locator circuit 327. Each acquisition circuit 325 also produces an event detection pulse ("EDP") which indicates the exact moment the scintillation event took place.

The event locator circuits 327 form part of a data acquisition processor 330, which periodically samples the signals produced by the acquisition circuits 325. The processor 330 has an acquisition CPU 329 which controls communications on local area network 318 and a backplane bus 331. The event locator circuits 327 assemble the information regarding each valid event into a set of digital numbers that indicate precisely when the event took place and the position of a crystal which detected the event. This event data packet is conveyed to a coincidence detector 332 which is also part of the data acquisition processor 330.

The coincidence detector 332 accepts the event data packets from the event locators 327 and determines if any two of them are in coincidence. Coincidence is determined by a number of factors. First, the time markers in each event data packet must be within a preset time of each other, and second, the locations indicated by the two event data packets must lie on a straight line. Events that cannot be paired are discarded, but coincident event pairs are located and recorded as a coincidence data packet.

The coincidence data packets are conveyed through a link 333 to a sorter 334 where they are used to form a sinogram. The sorter 334 forms part of an image reconstruction processor 340. The sorter 334 counts all events occurring along each projection ray (R, θ) and organizes them into a two dimensional sinogram array 348 which is stored in a memory module 343. In other words, a count at sinogram location (R, θ) is increased each time a coincidence data packet at that projection ray is received.

The image reconstruction processor 340 also includes an image CPU 342 that controls a backplane bus 341 and links it to the local area network 318. An array processor 345 also connects to the backplane 341 and it reconstructs an image from the sinogram array 348. The resulting image array 346 is stored in memory module 343 and is output by the image CPU 342 to the operator work station 315.

The image reconstruction processor 340 may be configured to process acquired PET data by analyzing the emission tomography data, in accordance with aspects of the present disclosure, to determine a concentration distribution of a tracer within the tissue. For example, the image reconstruction processor 340 may obtain a quantitative map of volume of distribution $V_d$ of a tissue by using Logan plot.

In some aspects, the image reconstruction processor 340 may be configured to access the emission data associated with the tissue; analyze the emission data to determine a concentration distribution of the tracer of the tissue of the subject; correlate the concentration distribution of the tracer with a membrane potential of the subject's tissue; and generate, using the correlation, a quantitative map of the membrane potential distribution of the subject's tissue.

In other aspects, the image reconstruction processor 340 may be configured to design a model by i) modeling a total volume of distribution of the tracer across the mitochondrial membrane and a cell membrane in an imaging voxel in relation with volume fractions of the extracellular space and the mitochondrial space, and electrical potentials across the mitochondrial membrane and the cell membrane; and ii) acquiring, using a medical imaging system, anatomical imaging data and using the anatomical imaging data to determine the volume fraction of the extracellular space associated with the tissue.

In other aspects, the image reconstruction processor 340 may be configured to design a model by reconstructing the emission tomography data into at least one emission tomography image; defining a voxel in the at least one emission tomography image to include an extracellular space and an intracellular space separated by a cell membrane; defining the extracellular space to include a mitochondrial membrane; defining the intracellular space to include a mitochondrial space and a cytosolic space; assuming the tracer in a steady state within the voxel; and relating the electrical potential across the mitochondrial membrane with a total volume of distribution in the voxel and the electrical potential across the cell membrane and the volume fraction of the extracellular space. Specifically, the image reconstruction processor 340 is configured to convert a quantitative map of volume of distribution $V_d$ into a quantitative map of the membrane potential distribution of the subject's tissue.

The operator work station 315 includes a CPU 350, a display 351 and a keyboard 352. The CPU 350 connects to the network 218 and it scans the keyboard 252 for input information. Through the keyboard 352 and associated control panel switches, the operator can control the calibration of the PET scanner and its configuration. Similarly, the operator can control the display of the resulting image on the display 351 and perform image enhancement functions using programs executed by the work station CPU 350.

In one aspect, the present disclosure discloses a system for quantitatively mapping membrane potential of a tissue in a subject. The system comprises an emission imaging system as discussed above. The system is configured to acquire emission data from the subject following an administration of a tracer. The system further comprises a processor configured to: 1) access the emission data associated with the tissue; 2) analyze the emission data to determine a concentration distribution of the tracer of the tissue of the subject; 3) correlate the concentration distribution of the tracer with a membrane potential of the subject's tissue; and 4) generate, using the correlation, a quantitative map of the membrane potential distribution of the subject's tissue.

In one implementation, the emission imaging system includes at least one of a positron emission tomography (PET) imaging system or a single photon emission computed tomography (SPECT) imaging system.

In another aspect, the present disclosure reveals a non-transitory, computer-readable storage medium having stored thereon instructions that, when executed by a computer processor, cause the computer processor to generate a report of quantitatively mapping membrane potential of a tissue in a subject by carrying out steps comprising: acquiring, using an emission tomography system, an emission data associated with the tissue; analyzing the emission data to determine a concentration distribution of a tracer of the tissue of the subject; correlating the concentration distribution of the tracer with membrane potential across membranes of the subject's tissue; and generating, using the correlation, a quantitative map of the membrane potential distribution of the subject's tissue.

EXAMPLES

Methods
  Theory
    When lipophilic cations with delocalized charges are introduced into the plasma of a living animal, they cross plasma and mitochondrial membranes and accumulate in the extracellular and intracellular spaces, due to the electrochemical gradient across the plasma and mitochondrial membranes. Membrane transport of $TPP^l$ depends on the existence of voltage-gated ion channels. Each voxel represents the state of millions of myocytes. PET images are also temporal averages spanning many cardiac cycles. The instantaneous current flowing in the voxel is thus time varying, periodically rising and falling as voltage-gated ion channels open and close. Bench top estimates of $\Delta\Psi_m$ made with cationic tracers universally rely on the Nernst equation to represent $\Delta\Psi_m$ in terms of the concentration ratio inside of versus outside of the membrane. In the parlance of electrophysiology, this voltage should be equal to the equilibrium potential. Thus, if one can use PET tracer methodology to estimate the equilibrium blood to tissue ratio, Applicants can apply the Nernst equation and some basic physiological concepts to estimate the membrane potential.

FIG. 5 shows the relationships of the distribution spaces for a conceptual PET image voxel. This highly simplified model is used to predict the concentrations of the subcellular compartments in terms of membrane potential and the fractional volumes of the constituents. Based on the measured specific activity of $^{18}F\text{-}TPP^+$ in tracer experiments, its typical molar concentration is between $10^{-10}$ and $10^{-7}$ times lower than the intracellular potassium concentration, meaning it is present in tracer amounts and its effect on membrane potential is thus negligible.

Consider the volume of distribution for $TPP^l$ implied in the schematic diagram shown in FIG. 5. The total volume of distribution is equal to the sum on the distribution volumes of the individual component parts, each weighted by its volume fraction. Accordingly, the model prediction for the total tissue concentration can be written as a weighted sum of the intracellular and extracellular concentrations where $f$ denotes a volume fraction and subscripts cell and ECV, refer to the cellular and extracellular volume components respectively. The cellular component can be approximated as the sum of mitochondrial $(_{mito})$ and cytosolic $(_{cyto})$ fractions. And so, the total concentration for the tissue volume can be represented symbolically by Equation 1.

Assuming that extracellular and plasma concentrations, $C_p$, are in equilibrium ($C_{ECV}=C_p$; Equation 2).

The Nernst equation applies to steady-state concentrations (rather than time-varying tracer concentrations) and relates the concentration ratios inside $C_{in}$ and outside $C_{out}$ to the membrane to the membrane potential $e^{\beta\Delta\Psi}=C_{in}/C_{out}$, where $\Delta\Psi$ is the voltage across the membrane and $\beta=zF/RT$ is a ratio of known physical parameters: F denotes Faraday's constant, z is the valence, R is the universal gas constant and T is the temperature in degrees Kelvin. Accordingly, the total volume of distribution in a PET voxel can be expressed as Equation 3, where $\Delta\Psi_m$ and $\Delta\Psi_c$ represent the electrical potential in mV across the mitochondrial and cell membranes respectively, with the electrical potential being negative inside the membrane. Equation 3 can also be generalized to account for additional mechanisms, such as nonspecific binding, as required.

Figure 6:
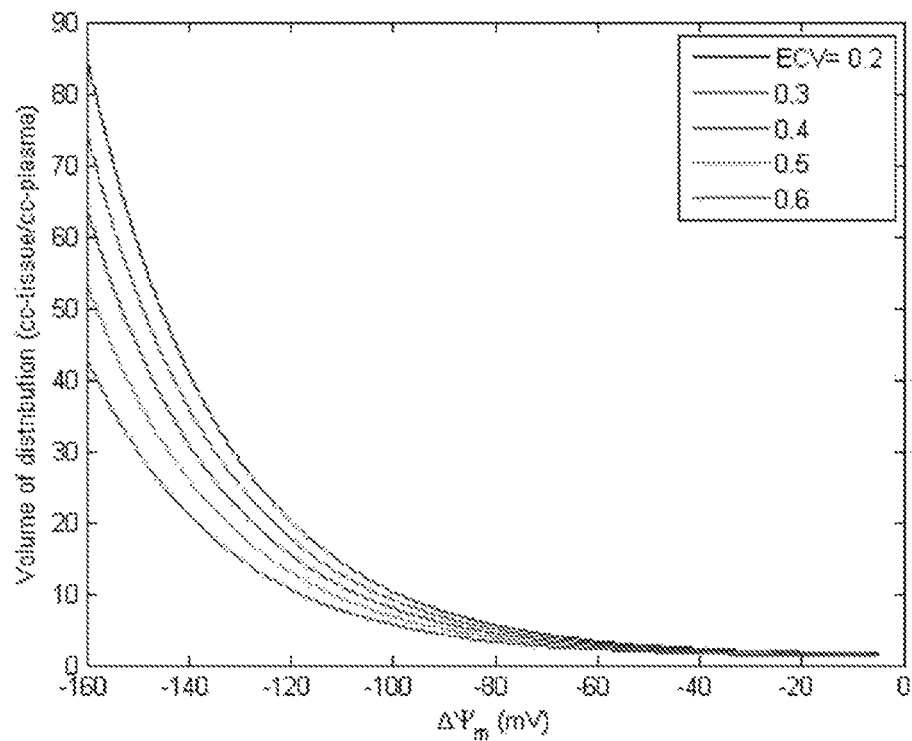
FIG. 6 is a graphical illustration showing volume of distribution of a tracer as a function of $\Delta\Psi_m$ and extracellular volume, in accordance with certain embodiments of the present disclosure.

Equation 3 predicts that the total volume of distribution for $^{18}F\text{-}TPP^+$ depends on the volume fractions of extracellular space, the mitochondrial and cell membrane potentials and the mitochondrial volume fraction, as graphed in FIG. 6. Visual inspection shows that correcting for changes in ECV at normal $\Delta\Psi_m$ is more important than when tissue is depolarized. Since $V_d$ can be measured directly by PET (Logan, Fowler et al. 1990; Zhou, Ye et al. 2009), Equation 3 can be used to infer $\Delta\Psi_m$ provided that estimates for the volume fractions and cellular membrane potential are available.

Animal Preparation

Study Cohort

The study cohort consisted of n=9 domestic swine which were divided into two groups, control (n=6) and tissue injury (scar) (n=3). The injury group received an experimentally induced injury to the myocardial tissue supplied by the left anterior descending artery resulting in infarction in the apical septal segments. Pigs were housed and maintained under the supervision of the Massachusetts General Hospital Animal Care and Use Committee. Studies were conducted serially, one pig at a time, from August 2014 till October 2015. The weight of the pigs at scan averaged 53.1 kg with a range from 30-92 kg.

Nine $^{18}$F-TPP$^+$ studies were performed, six of them in a control state, anesthetized but without tissue injury and three studied about three weeks after experimentally induced infarction. Pigs were fasted 12 hours prior to induction of anesthesia, sedated with 4.4 mg/kg Telazol, placed on 5% masked isoflurane, intubated, maintained with 1.5% isoflurane and mechanically ventilated. Vital signs were monitored continuously. Vascular access was obtained via the femoral veins for injection of PET radiotracer and iodinated contrast media. An arterio-venous shunt was placed in the left femoral artery for blood withdrawal.

The following procedure was followed to infarct the left anterior descending (LAD) territory: Percutaneous central access was achieved via the Seldinger technique. Femoral artery access was obtained and a guide wire was advanced into the left LAD coronary artery. A balloon catheter was then fed over the guidewire and placed in the middle of the LAD and inflated to 6-8 atm for 80 minutes. An infarct was noted by the appearance of large ST elevation on ECG. After this procedure pigs were allowed to recover for three weeks before PET/CT scanning.

Blood Sampling

Arterial blood sampling of $^{18}$F-TPP$^+$ were drawn every 10 seconds for the first 3 minutes, then at 1 minute intervals for 5 minutes, and at increasing intervals until 120 minutes post injection. In two studies, venous several blood samples were also drawn at 5, 10, 15, 30, 60 and 90 minutes for comparison with arterial samples. All blood samples were centrifuged to determine plasma and red cell concentration histories. Concentration ratios of whole blood to plasma were computed.

PET Scanning

PET Scans were performed on a Siemens Biograph PET/CT scanner: A planar x-ray topogram was performed to define the field of view (FOY) with the heart centered for computed tomography (CT), CT-angiogram (CTA) and PET acquisitions. The cardiac CT and CTA studies were used for anatomic reference and the CT was also used for attenuation correction during reconstruction of PET images. PET list mode acquisition was started just before the injection of $^{18}$F-TPP$^+$ and continued for a duration of 60 minutes. List mode data were framed as a dynamic series of 12×3, 9×5, 7×10, 15×30 second frames. Each frame was reconstructed using a filtered back projection algorithm to yield a radioactivity concentration map in units of Bq/cc with 83 slices and a voxel size of 2.14×2.14×3 mm$^3$.

Measurement of Extracellular Volume

Measurements of the fractional ECV were made using CT scanning (Siemens Biograph 64) and a bolus and infusion protocol (Bandula, White et al. 2013). A bolus of iohexole at a concentration of 1 mL/kg of body weight was followed by an infusion with concentration 1.88 mL/kg/h for the infusion using a power injector (Medrad, Warrendale, Pa.) for the administration of the bolus and a syringe pump for the infusion (Medfusion, Cary, N.C.). CT images were acquired before contrast was administered and 15 min after the start of the iodine injection. The ECV fraction was calculated as $$ECV=(1-H_{ct})\cdot[(HU_{post}-HU_{pre})_{tissue}/[(HU_{post}-HU_{pre}]_{pre},$$

where $HU_{post}$ and $HU_{pre}$ are the CT numbers in Hounsfield units, post- and pre-contrast respectively. For the blood, Hounsfield Units were obtained using an ROI of $\sim$2×2×3 cm$^3$ in the left ventricular chamber. CT imaging parameters were as follows: tube voltage, 120 kV; tube current, 308 mA; matrix size, 512×512×146 and voxel size 0.39*0.39*1 mm. CT images were resliced to match the PET voxel size and smoothed with a 2.14 mm (sigma) gaussian filter before calculation of the ECV fraction.

The extracellular volume was measured in three pigs with experimentally induced tissue injury using iodinated contrast material and CT scanning, yielding estimates of ECV for injured and uninjured myocardium.

Data Analysis

ECV maps were analyzed in the short axis projection, partitioning the LV myocardium from apex to base into 17 bull's eye segments. Average values of ECV were computed by segment.

Dynamic PET data were analyzed using a Logan plot (Logan, Fowler et al. 1990) to produce parametric images of the $^{18}$F-TPP$^+$ volume of distribution, $V_d$ and reoriented into the short axis projection. In the calculation of $V_d$, Applicants estimated the plasma concentration directly from the PET scans by sampling the LV chamber with an ROI. Equation 4 was used to convert the parametric maps of $V_d$ to maps of $\Delta\Psi_m$, assuming $\Delta\Psi_c=-30$ mV and $f_{mito}=0.15$.

Results

Blood sampling showed that the concentration ratio for whole blood versus plasma became constant at 0.95 about 10 minutes after injection of TPP$^|$ and remained so for the duration of measurement (120 minutes). Venous and arterial samples obtained at least 10 minutes after injection of TPP$^+$ were in good agreement.

Figure 7:
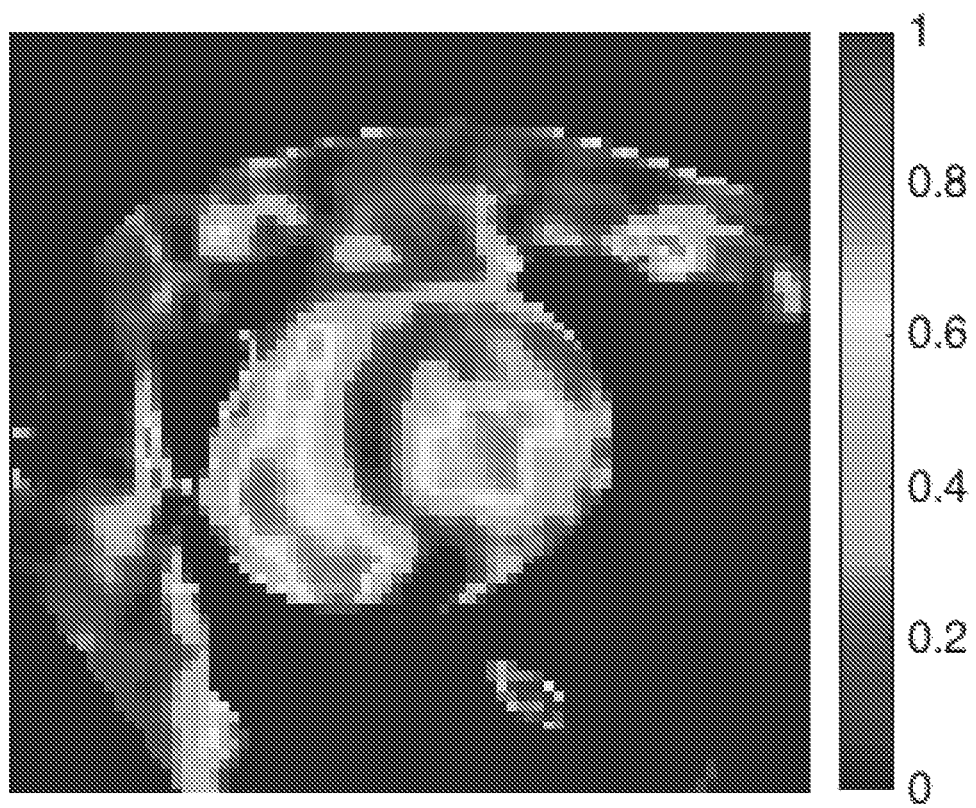
FIG. 7 is a photo depicting representative ECV maps in the short axis view for a healthy pig, in accordance with certain embodiments of the present disclosure.
Figure 10:
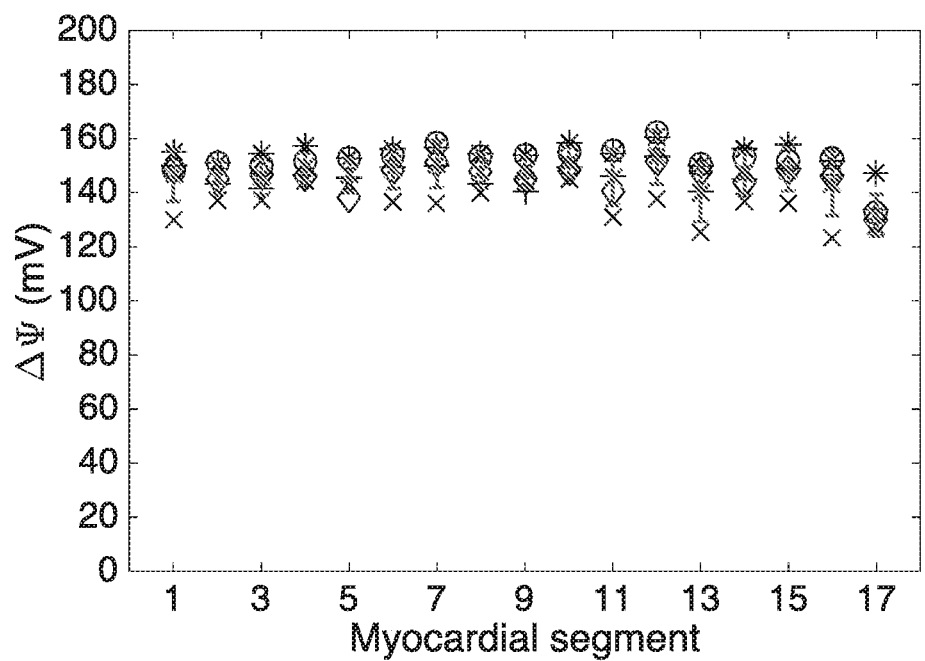
FIG. 10 is a graphical illustration showing membrane potential $\Delta\Psi$ values for 5 healthy pigs in each of the 17 segments, processed in accordance with aspects of the present disclosure. Red marks show mean±1 SD across the pigs.

FIG. 7 shows a representative ECV map for a slice in short axis view in healthy tissue. FIG. 8 shows an example of a parametric map of $V_d$ in a pig with experimental tissue injury in the LAD territory. The data are shown in three projections, short axis, horizontal and vertical long axis projections. $V_d$ ranges from a low value of 2 mL/cc in the core of the injury (see arrows) to 25 mL/cc in areas in other vascular territories. FIG. 9 shows the corresponding map of mitochondrial membrane potential. Inspection of FIG. 9 shows that $\Delta\Psi_m$ varies from 20 mV in the core of the tissue injury to 145 mV in other vascular territories. FIG. 10 shows the values of $\Delta\Psi_m$ for the five pigs in each of 17 segments.

Administration Methods

Applicants show that the measured concentration ratio is a function of mitochondrial membrane potential, the fraction of tissue occupied by the extracellular space, the fraction of the cell volume occupied by mitochondria and the electrical potential across the cell membrane. Because of the thermodynamic and chemical nature of the Nernst equation, the results describe relationships that only hold when the reactants are in steady state.

Figure 11:
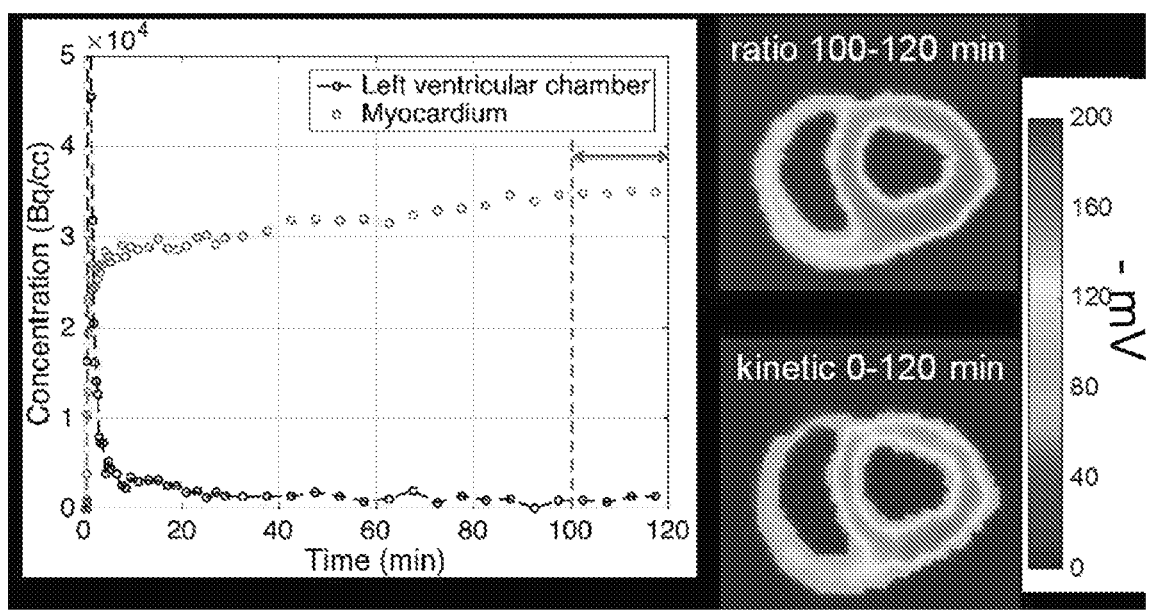
FIG. 11 is a set of graphs and photos showing concentration versus time of $^{18}$F-TPP$^+$ and the as-measured $\Delta\Psi_m$ distribution among the heart in a normal domestic swine.

Applicants use a few administration methods including a constant infusion, a pulse or bolus injection or a combination of a constant infusion a pulse or bolus injection. To date, most of Applicants work has used the kinetic approach because it carries the complete information available from our measurements. By analyzing the kinetic data (concentration vs time), Applicants can infer the steady state based on the ratio of the tissue concentration to the plasma concentration. FIG. 11 shows the result of an experiment in which Applicants administered the tracer intravenously as pulse of TPP$^+$ followed by a constant infusion of the tracer. The addition of the pulse or bolus injection to the constant infusion can shorten the time needed to impose the steady state for TPP$^+$. In this case both the plasma and myocardial concentrations become constant after about 90 minutes. The two color pictures are from studies in the same pig but measured on different days, one using constant infusion and the other the kinetic protocol. Note the excellent agreement between the two methods.

Discussion

This is the first research report discussing quantitative mapping of the mitochondrial membrane potential. The mapping provides a three-dimensional pictorial representation but importantly the intensities are in absolute units, mV. The underlying theory relies on well-accepted tracer kinetic principles and the Nernst equation, a pillar of electrochemistry (Bockris and Reddy 2012) and cardiac electrophysiology (Whalley, Wendt et al. 1995; Iwai, Markowitz et al. 2013). Applicants partitioned tracer distribution within a PET image voxel (FIG. 5), deriving an equation that predicts the magnitude of the measured volume of distribution of lipophilic cationic tracers in terms of several physiological parameters: (1) mitochondrial membrane potential, (2) the fractional volume occupied by the extracellular volume, (3) the cellular membrane potential and (4) the fractional volume occupied by the mitochondria. The relation among these quantities is illustrated graphically in FIG. 6.

Applicants note that there is a great similarity between Applicants' PET method and the highly invasive bench top methods which preceded it. But there are differences, too. In the classical methods, applied to ensembles of cells in culture medium or the isolated perfused rat heart models, the cells and hearts are not spontaneously beating; there are no transient electrical currents similar to the action potentials which propagate cyclically over the atria and ventricles of a beating heart. Thus, a steady state assumption is reasonable. The tracer concentration in a PET image voxel represents an average over millions of myocytes and fibroblasts, a complexity which Applicants did not address. Applicants also recognize the distribution of ions in myocardial tissue is not invariant with time but nevertheless assume that the time-averaging inherent in the PET measurement procedures which occur on the scale of minutes is sufficient to approximate a steady state.

There are other assumptions in the PET method which are also common to the classical methods. For example, Applicants assumed that the fraction of mitochondria per cc of myocardial tissue is known and a constant. Prior studies with $^3$H-TPP$^+$ have sometimes made corrections for non-specific binding of TPP$^+$. Similar corrections could be applied to the PET analyses, but were unnecessary to establish initial feasibility. Applicants note in the experimental scar model that $\Delta\Psi_m$ is dramatically reduced, as might be expected.

Some investigators have assumed that $^{18}$F-TPP$^+$ was a tracer of myocardial blood flow because of its high myocardial uptake, but prior work with $^3$H-TPP$^+$ in isolated rat heart model demonstrated slow kinetics in bench top studies, inconsistent with application to flow measurements. To provide a direct observation Applicants compared the kinetics of $^{18}$F-TPP$^+$ to those of $^{18}$F-Flurppiridaz, a tracer with high first pass capillary extraction (E>0.9). The results, presented in FIG. 4, clearly show that the extraction of TPP$^+$ is much lower, and that tracer accumulates slowly in the myocardium. Thus it is unlikely that TPP$^+$ can provide useful myocardial flow measurements, per se.

The quantitative values of myocardial mitochondrial membrane potential measured in Applicants' studies agree with the result of previous measurements, as shown in Table 1. To the degree that it makes sense to compare Applicants in vivo measurements made in domestic swine to cell culture and isolated heart preparations, the PET method yields results that are very close to those found by Wan et al. Applicants give less weight to the results obtained by Fukuda about 30 years ago in a canine model using an early PET camera whose quantitative capability was relatively poor. Finally, Applicants note the results of Gurm, et al, which are not in line with the other reports or the present work.

TABLE 1

The result of previous measurements of $\Delta\Psi_m$.

| Authors | Preparation | Tracer | $\Delta\Psi_m$ (mV) |
|---|---|---|---|
| Kauppinen, (Kauppinen 1983) | perfused rat hearts | $^3$H-TPMP$^+$ | 125 |
| Rottenburg,) (Rottenberg 1984) | rat liver | $^3$H-TPP$^-$ | 150 |
| Fukuda, et al (Fukuda, Syrota et al. 1986) | in vivo dog heart | $^{11}$C-TPMP+ | 148 |
| LaNoue, et al (LaNoue, Strzelecki et al. 1986, Fahmy, Wazni et al. 2008) | isolated brown adipocytes | $^3$H-TPP$^-$ | 116 |
| Wan, et al (Wan, Doumen et al. 1993) | perfused rat hearts | $^3$H-TPP+ | 145[1] 118[2] |
| Gurm, et al (Gurm, Danik | in vivo swine | $^{18}$F-TPP$^+$ | 91 |

This study demonstrates the basic feasibility of quantitative mapping of $\Delta\Psi_m$. Recognizing that further validation and experience are needed, it is reasonable to speculate on the possibilities for clinical translation. One of the most obvious applications is to cardiac electrophysiology: Catheter ablation, the standard of care for complex arrhythmias, particularly ventricular tachycardia (VT) (Strickberger, Man et al. 1997) is guided by electroanatomic mapping (EAM) which involves roving catheter contact with the myocardial surface to record local electrograms. When combined by a 3-dimensional mapping system, these electrograms allow the creation of maps demonstrating normal and abnormal myocardium as well as scar. But EAM has limitations that might be overcome using mapping of $\Delta\Psi_m$ which is essentially noninvasive. Maps of $\Delta\Psi_m$ could be obtained prior to EAM and serve as a road map for the electrophysiologist, allowing more detailed investigation. Unlike EAM which is sensitive to current flowing near the surfaces of the myocardium, the PET method should be sensitive to abnormalities in $\Delta\Psi_m$ at any depth in myocardial thickness. The use of the new modality of PET/MR could also be used while mapping $\Delta\Psi_m$ to remove motion blurring due to respiration and cardiac function by which it should be possible to achieve $\Delta\Psi_m$ maps with 3-4 mm resolution. Previous work used functional endpoints such as blood flow, or glucose utilization in an effort to detect injured but viable myocardium. $\Delta\Psi_m$ is distinctly different; it directly assesses the ability of tissue to support conduction. When myocytes experience infarction or ischemia, there is either complete or partial depolarization of those cells, resulting in a reduced membrane potential. When the cell is partially depolarized, action potentials are distorted, causing local changes in rhythm, or disruptions or blockage of conductance and arrhythmia, not only can PET MP mapping address many of the limitations of EAM, there is the additional possibility for monitoring after both ablation and pharmacological therapies.

Conclusions

Applicants have developed the first minimally invasive, low risk method for quantitative mapping of mitochondrial membrane potential of the beating heart. With further development and validations, the method is suitable for clinical translation.

The present invention has been described in terms of one or more preferred embodiments, and it should be appreciated that many equivalents, alternatives, variations, and modifications, aside from those expressly stated, are possible and within the scope of the invention.

We claim:

1. A method for quantitatively mapping mitochondrial membrane potential of an in vivo tissue in a subject, the method comprising:
   a) administering to the subject a detectably effective amount of $^{18}$F-tetraphenylphosphonium ($^{18}$F-TPP$^+$) as an emission tomography imaging agent;
   b) acquiring, using an emission tomography system, emission tomography data associated with the tissue;
   c) analyzing the emission tomography data to determine a concentration distribution of $^{18}$F-TPP$^+$ within the tissue;
   d) correlating the concentration distribution of $^{18}$F-TPP$^+$ with the mitochondrial membrane potential of the tissue, comprising the steps of:
      i) modeling a total volume of distribution of a plurality of spaces across the mitochondrial membrane and a cell membrane in an image voxel in relation with volume fractions of the plurality of spaces, and electrical potentials across the mitochondrial membrane and the cell membrane; and
      ii) acquiring, using a medical imaging system, anatomical imaging data and using the anatomical imaging data to determine volume fractions of the plurality of spaces associated with the tissue;
   e) determining, based on the correlation at step d), a membrane potential distribution of the tissue; and
   f) generating a report indicating the membrane potential distribution of the tissue.

2. The method of claim 1, wherein the plurality of spaces includes an extracellular space and an intracellular space separated by a mitochondrial membrane wherein the extracellular space includes a plasma membrane and the intracellular space includes a mitochondrial space and a cytosolic space.

3. A method for quantitatively mapping membrane potential of a tissue in a subject, the method comprising:
   a) administering to the subject a detectably effective amount of a radioactive tracer;
   b) acquiring, using an emission tomography system, emission tomography data associated with the tissue;
   c) analyzing the emission tomography data to determine a concentration distribution of the radioactive tracer within the tissue;
   d) correlating, using a model, the concentration distribution of the radioactive tracer with the membrane potential of the tissue;
   e) determining, based on the correlation at step d), a membrane potential distribution of the tissue; and
   f) generating a report indicating the membrane potential distribution of the tissue.

4. The method of claim 3, wherein step (b) begins at least one of:
   before the administration of the tracer and continues for a first duration of time;
   after the administration of the tracer; or
   about 100 minutes after the administration of the tracer.

5. The method of claim 3, wherein the tracer is $^{18}$F-tetraphenylphosphonium ($^{18}$F-TPP$^+$).

6. The method of claim 3, wherein the tissue is associated with at least one of a heart, skeletal muscle, liver, kidney, or tumor.

7. The method of claim 3, wherein the membrane potential is a mitochondrial membrane potential.

8. The method of claim 3, wherein the method further comprises generating the model by:
   reconstructing the emission tomography data into at least one emission tomography image;
   defining each image voxel in the at least one emission tomography image to include an extracellular space component and an intracellular space component separated by a mitochondrial membrane component;
   defining the extracellular space component to include a cell membrane component;
   defining the intracellular space component to include a mitochondrial space component and a cytosolic space component; and
   relating the electrical potential across the mitochondrial membrane with a total volume of distribution in each image voxel and the electrical potential across the extracellular space volume.

9. The method of claim 8, further comprising
   acquiring, using a medical imaging system, anatomical imaging data and using the anatomical imaging data to determine a volume distribution of different spaces associated with the tissue.

10. The method of claim 8, wherein the model includes:
    $V_d = (1-f_{ECV})(f_{mito} \cdot e^{-\beta(\alpha\Psi m + \alpha\Psi c)} + (1-f_{mito}) \cdot e^{-\beta\alpha\Psi c}) + f_{ECV}$,
    wherein $V_d$ represents the total volume of distribution of the tracer in the imaging voxel;
    $f_{ECV}$ represents a volume fraction of the extracellular space;
    $f_{mito}$ represents a volume fraction of the mitochondrial space; $\alpha\Psi m$ and $\alpha\Psi c$ represent the electrical potential across the mitochondrial and cell membranes, respectively.

11. The method of claim 8, wherein the method further comprises:
    measuring the volume fraction of the extracellular space $f_{ECV}$.

12. The method of claim 8, wherein the method further comprises the steps of:
    estimating the volume fraction of the mitochondrial space; and
    estimating the electrical potential across the cell membrane.

13. A method for identifying a disease condition of a subject, the method comprising:
    i) administering to the subject a detectably effective amount of a tracer;
    ii) acquiring, using an emission tomography imaging system, emission tomography data and analyzing the emission tomography data to determine a concentration distribution of the tracer of a tissue of the subject;
    iii) correlating the concentration distribution of the tracer with a membrane potential of the subject's tissue;
    iv) processing the emission tomography data to generate a quantitative map of the membrane potential distribution of the subject's tissue; and v) generating a report indicative of the disease condition of the subject.

14. The method of claim 13, wherein step (ii) begins at least one of:
   before the administration of the tracer and continues for a first duration of time;
   after the administration of the tracer; or
   about 100 minutes after the administration of the tracer.

15. The method of claim 13, wherein the tracer is a lipophilic cation.

16. The method of claim 15, wherein lipophilic cation is $^{18}F$-tetraphenylphosphonium ($^{18}F$-TPP$^+$) at concentrations across membranes of the tissue in thermodynamic equilibrium.

17. The method of claim 13, further comprising correlating the concentration distribution of the tracer with a membrane potential of the subject's tissue by using an equation of
$$V_d = (1-f_{ECV})(f_{mito} \cdot e^{-\beta(\alpha\Psi m + \alpha\Psi c)} + (1-f_{mito}) \cdot e^{-\beta\alpha\Psi c}) + f_{ECV},$$
wherein $V_d$ represents the total volume of distribution of the tracer in the imaging voxel;
$f_{ECV}$ represents a volume fraction of the extracellular space;
$f_{mito}$ represents a volume fraction of the mitochondrial space; $\alpha\Psi m$ and $\alpha\Psi c$ represent the electrical potential in mV across the mitochondrial and cell membranes, respectively.

18. The method of claim 17, further comprising measuring the volume fraction of the extracellular space using imaging data acquired using at least one of a magnetic resonance imaging (MRI) system or a computed X-ray tomography (CT) system.

19. The method of claim 13, wherein the tissue is at least one of heart, skeletal muscle, liver, kidney, or tumor.

20. A system for quantitatively mapping membrane potential of a tissue in a subject, the system comprising:
   an emission imaging system configured to acquire emission data from the subject following an administration of a tracer; and
   a processor configured to:
   1) access the emission data associated with the tissue;
   2) analyze the emission data to determine a concentration distribution of the tracer of the tissue of the subject;
   3) correlate the concentration distribution of the tracer with a membrane potential of the subject's tissue; and
   4) generate, using the correlation, a quantitative map of the membrane potential distribution of the subject's tissue.

* * * * *

UNITED STATES PATENT AND TRADEMARK OFFICE
CERTIFICATE OF CORRECTION

PATENT NO. : 11,109,819 B2
APPLICATION NO. : 16/092650
DATED : September 7, 2021
INVENTOR(S) : Nathaniel M. Alpert et al.

It is certified that error appears in the above-identified patent and that said Letters Patent is hereby corrected as shown below:

In the Specification

Column 4, Line 43, "lip ophilic" should be --lipophilic--.

Column 4, Lines 58-59, "$V_d=(1-f_{ECV})(f_{mito}\cdot e^{-\beta(\Delta\Psi m+\Delta\Psi}c)+(1-f_{mito})\cdot e^{-\beta\Delta\Psi}c)+f_{ECV}$" should be --$V_d=(1-f_{ECV})(f_{mito}\cdot e^{-\beta(\Delta\Psi m+\Delta\Psi c)}+(1-f_{mito})\cdot e^{-\beta\Delta\Psi c})+f_{ECV}V$--.

Column 9, Line 50, "$^{18}F\text{-}TPP^|$" should be --$^{18}F\text{-}TPP^+$--.

Column 9, Line 55, "Cl" should be --Cl⁻--.

Column 10, Line 8, "$TPP^|$" should be --$TPP^+$--.

Column 12, Line 16, "(b 1)" should be --(1)--.

Column 12, Lines 30-31, "$V_d=(1-f_{ECV})(f_{mito}\cdot e^{-\beta}(\Delta\Psi m+\Delta\Psi c)+(1-f_{mito})\cdot e^{-\beta\Delta\Psi}c)+f_{ECV}$" should be --$V_d=(1-f_{ECV})(f_{mito}\cdot e^{-\beta(\Delta\Psi m+\Delta\Psi c)}+(1-f_{mito})\cdot e^{-\beta\Delta\Psi c})+f_{ECV}$--.

Column 12, Line 64, "(1-H_{ct})" should be --(-1Hct)--.

Column 19, Line 51, "(FOY)" should be --(FOV)--.

Column 20, Line 8, "(1-H_{ct})" should be --(1-Hct)--.

In the Claims

Column 24, Claim 10, Lines 37-38, "$V_d=(1-f_{ECV})(f_{mito}\cdot e^{-\beta(\alpha\Psi m+\alpha\Psi c)}+(1-f_{mito})\cdot e^{-\beta\alpha\Psi c)+f_{ECV}}$" should be --$V_d=(1-f_{ECV})(f_{mito}\cdot e^{-\beta(\Delta\Psi m+\Delta\Psi c)}+(1-f_{mito})\cdot e^{-\beta\Delta\Psi c})+f_{ECv}$--.

Column 24, Claim 10, Line 43, "α$\Psi$m and α$\Psi$c" should be --Δ$\Psi$m and Δ$\Psi$c--.

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*

Column 25, Claim 17, Line 18-19, "$V_d=(1-f_{ECV})(f_{mito}\cdot e^{-\beta}(\alpha\Psi m+\alpha\Psi c)+(1-f_{mito})\cdot e^{-\beta\alpha\Psi c})+f_{ECV}$" should be --$V_d=(1-f_{ECV})(f_{mito}\cdot e^{-\beta(\Delta\Psi m+\Delta\Psi c)}+(1-f_{mito})\cdot e^{-\beta\Delta\Psi c})+f_{ECV}$--.

Column 25, Claim 17, Line 24, "$\alpha\Psi m$ and $\alpha\Psi c$" should be --$\Delta\Psi m$ and $\Delta\Psi c$--.